(12) United States Patent
Melodia et al.

(10) Patent No.: US 11,826,119 B2
(45) Date of Patent: *Nov. 28, 2023

(54) INTERNET-LINKED ULTRASONIC NETWORK FOR MEDICAL DEVICES

(71) Applicant: Northeastern University, Boston, MA (US)

(72) Inventors: Tommaso Melodia, Newton, MA (US); Giuseppe Enrico Santagati, Cambridge, MA (US)

(73) Assignee: Northeastern University, Boston, MA (US)

( * ) Notice: Subject to any disclaimer, the term of this patent is extended or adjusted under 35 U.S.C. 154(b) by 266 days.

This patent is subject to a terminal disclaimer.

(21) Appl. No.: 17/104,349

(22) Filed: Nov. 25, 2020

(65) Prior Publication Data

US 2021/0076937 A1 Mar. 18, 2021

Related U.S. Application Data

(63) Continuation of application No. 15/546,423, filed as application No. PCT/US2016/014860 on Jan. 26, 2016, now Pat. No. 10,849,503.

(Continued)

(51) Int. Cl.
*A61B 5/00* (2006.01)
*H04B 11/00* (2006.01)
(Continued)

(52) U.S. Cl.
CPC .......... *A61B 5/0015* (2013.01); *A61B 5/0024* (2013.01); *A61B 5/0026* (2013.01);
(Continued)

(58) Field of Classification Search
CPC ... A61B 5/0015; A61B 5/0028; A61B 5/0024; A61B 5/0026; A61B 5/02438;
(Continued)

(56) References Cited

U.S. PATENT DOCUMENTS 6,695,885 B2 2/2004 Schulman et al.
7,733,224 B2 6/2010 Tran
(Continued)

OTHER PUBLICATIONS

Anonymous, "Introducing the Internet Protocol Suite (System Administration Guide, vol. 3)", Dec. 31, 2010, XP055917362, Retrieved from the Internet: URL:https://docs.oracle/com/cd/E19455-01/806-0916/6ja85398m/index.html[retrieved on May 3, 2022].

(Continued)

*Primary Examiner* — Mark W. Bockelman
(74) *Attorney, Agent, or Firm* — Verrill Dana, LLP

(57) ABSTRACT

A system and method is provided for transmitting signals ultrasonically among a network of implantable and wearable biological devices. The devices includes one or more implantable nodes, which include a sensing and/or actuating unit, at least one gateway node, and at least one access point node. Ultrasonic signals can be transmitted through the body by the implantable nodes to and from the gateway node, for transmission to and from the access point node. The access point node can be connected to the Internet. In this manner, remote instructions can be transmitted to the implantable nodes and data obtained at the implantable nodes can be transmitted to remote sites.

15 Claims, 18 Drawing Sheets

Related U.S. Application Data

(60) Provisional application No. 62/107,737, filed on Jan. 26, 2015.

(51) Int. Cl.
   *G16H 40/63* (2018.01)
   *H04W 84/18* (2009.01)
   *A61B 5/0205* (2006.01)
   *A61B 5/024* (2006.01)

(52) U.S. Cl.
   CPC ........... *A61B 5/0028* (2013.01); *G16H 40/63* (2018.01); *H04B 11/00* (2013.01); *H04W 84/18* (2013.01); *A61B 5/0205* (2013.01); *A61B 5/02438* (2013.01)

(58) Field of Classification Search
   CPC ..... A61B 5/0205; H04B 11/00; H04W 84/18; G16H 40/63
   See application file for complete search history.

(56) References Cited

U.S. PATENT DOCUMENTS

| | | | |
|---|---|---|---|
| 8,301,232 | B2 | 10/2012 | Albert et al. |
| 8,509,882 | B2 | 8/2013 | Albert et al. |
| 9,451,340 | B2 | 9/2016 | Duesterhoft et al. |
| 9,514,066 | B1 | 12/2016 | Diaz et al. |
| 10,849,503 | B2 * | 12/2020 | Melodia ............... A61B 5/0024 |
| 2004/0015079 | A1 | 1/2004 | Berger et al. |
| 2004/0202339 | A1 | 10/2004 | O'Brien, Jr. et al. |
| 2006/0224048 | A1 | 10/2006 | Devaul et al. |
| 2010/0298669 | A1 | 11/2010 | Ida |
| 2013/0197320 | A1 | 8/2013 | Albert et al. |
| 2013/0274563 | A1 | 10/2013 | Duesterhoft et al. |
| 2014/0128754 | A1 | 5/2014 | Luna et al. |
| 2014/0206976 | A1 | 7/2014 | Thompson et al. |
| 2015/0018660 | A1 | 1/2015 | Thomson et al. |
| 2015/0261415 | A1 | 9/2015 | Lee et al. |
| 2016/0174158 | A1 | 6/2016 | Vance et al. |
| 2017/0284859 | A1 | 10/2017 | Bauer et al. |
| 2017/0284920 | A1 | 10/2017 | Bauer et al. |

OTHER PUBLICATIONS

Galluccio, L. et al., "Challenges and Implications of Using Ultrasonic Communications in Intra-body Area Networks", 2012 9th Annual Conference on Wireless On-Demand Network Systems and Services (WONS), Jan. 9, 2012, pp. 182-189.

Santagati, G.E. et al., "Sonar Inside Your Body: Prototyping Ultrasonic Intra-body Sensor Networks", IEEE INFOCOM 2014—IEEE Conference on Computer Communications, Apr. 27, 2014, pp. 2679-2687.

* cited by examiner

INTERNET-LINKED ULTRASONIC NETWORK FOR MEDICAL DEVICES

CROSS REFERENCE TO RELATED APPLICATIONS

This application claims benefit under 35 U.S.C. § 120 of U.S. patent application Ser. No. 15/546,423, filed on 26 Jul. 2017, entitled "Internet-Linked Ultrasonic Network for Medical Devices," which is a national phase entry of International Application No. PCT/US2016/014,860, filed on 26 Jan. 2016, entitled "Internet-Linked Ultrasonic Network," which claims priority under 35 § 119(e) of U.S. Provisional Application No. 62/107,737 filed on 26 Jan. 2015, entitled "U-Wear: Software-Defined Ultrasonic Networking for Wearable Devices", the disclosures of all of which are hereby incorporated by reference.

STATEMENT REGARDING FEDERALLY SPONSORED RESEARCH OR DEVELOPMENT

The invention was developed with financial support from Grant No. CNS-1253309 from the National Science Foundation. The U.S. Government has certain rights in the invention.

BACKGROUND

Wearable medical sensing devices with wireless capabilities have become the cornerstone of many digital health applications that promise to predict and treat major diseases by acquiring and processing health information. Existing wireless wearable devices are connected through radio frequency processing (RF) electromagnetic wave carriers based on standards such as Bluetooth or Wi-Fi. However, these solutions tend to scale down traditional wireless technologies to the body environment, with little or no attention paid to the peculiar characteristics of the human body and the privacy and security requirements of patients.

SUMMARY OF THE INVENTION

An Internet-linked network of implantable and wearable devices is provided that uses an ultrasonic communication platform to provide control of biological parameters and procedures. More particularly, a system and method are provided for transmitting signals ultrasonically among a network of implantable and wearable biological devices, including one or more implantable nodes, at least one gateway node, and at least one access point node, which can provide for remote measurement, storage, and management of biological data and control of biological procedures and flexible configurability of the devices.

Other aspects of the method and system include the following:
1. A system for transmitting signals ultrasonically among a network of implantable and wearable biological devices, comprising:
    an implantable node, implantable in a body, comprising a sensing unit or an actuating unit, an ultrasonic communication interface operative to transmit and receive ultrasonic signals through biological tissue, and a core unit in communication with the communication interface and with the sensing unit or actuating unit;
    a gateway node wearable on the body, comprising an ultrasonic communication interface operative to transmit and receive ultrasonic signals through biological tissue and to transmit and receive ultrasonic signals through air, and a core unit in communication with the communication interface; and
    an access point node, including an ultrasonic communication interface operative to transmit and receive ultrasonic signals transmitted through air from at least the gateway node.
2. The system of item 1, further comprising an intra-body network of implantable nodes, each implantable node of the network comprising a sensing unit or an actuating unit, and an ultrasonic communication interface operative to transmit and receive ultrasonic signals through biological tissue.
3. The system of item 2, wherein a first implantable node includes a sensing unit, and a second implantable node includes an actuating unit, and the first implantable node and the second implantable nodes are in ultrasonic communication, whereby the actuating unit is actuable in response to data obtained by the sensing unit.
4. The system of any of items 1-3, wherein the core unit comprises one or more logic devices to control the sensing unit or the actuating unit.
5. The system of item 1-4, wherein the one or more logic devices include small-scale integrated circuits, programmable logic arrays, programmable logic device, masked-programmed gate arrays, field programmable gate arrays, and application specific integrated circuits.
6. The system of any of items 4-5, wherein the one or more logic devices include arithmetic logic blocks, registers, finite state machines, multiplexers, accumulators, counters, and look-up tables.
7. The system of any of items 1-6, wherein the core unit of one or both of the implantable node and the gateway node comprises a microcontroller unit and a field programmable gate array (FPGA) operative to execute communication, processing and networking tasks.
8. The system of item 7, wherein the core unit includes one or both of a serial peripheral interface (SPI) and an inter integrated circuit (I2C) interface to control communications between the microcontroller, the FPGA, the communications interface, the sensing unit or actuating unit, and memory.
9. The system of any of items 7-8, wherein the microcontroller unit is operative at upper layers of a protocol stack to enable ultrasonic communication.
10. The system of any of items 7-9, wherein the microcontroller unit is operative at one or more of a data link layer, a network layer, a transport layer, and an application layer of a protocol stack to enable ultrasonic communication.
11 The system of any of items 7-10, wherein the microcontroller unit is operative at the data link layer to provide forward error correction.
12. The system of any of items 7-11, wherein the microcontroller is operative at the data link layer to provide medium access control.
13. The system of any of items 7-12, wherein the microcontroller is operative at the network layer to provide content centric addressing.
14. The system of any of items 7-13, wherein the microcontroller is operative at the network layer to provide IP header compression and IP Packet fragmentation.
15. The system of any of items 7-14, wherein the microcontroller unit includes a real time operating system.

16. The system of any of items 7-15, wherein the FPGA is operative at a physical layer of a protocol stack to enable ultrasonic communication.
17. The system of any of items 7-16, wherein the FPGA is operative to modulate a bit stream from the microcontroller and pass the modulated bit stream to a digital-to-analog converter of the communication interface.
18. The system of any of items 7-17, wherein the FPGA is operative to demodulate an incoming digital signal from the communications interface and to perform synchronization and channel estimation signal processing on the incoming digital signal.
19. The system of any of items 7-18, wherein the FPGA is operative to perform correlation, Fourier transform or inverse Fourier transform, or filtering operations on a digital signal.
20. The system of any of items 7-19, wherein the FPGA includes a first-in-first-out memory queue to buffer incoming and outgoing data.
21. The system of any of items 7-20, wherein the FPGA includes a phase-locked loop module to synthesize clock signals with a higher or lower frequency than a system clock.
22. The system of any of items 7-21, wherein the FPGA is programmable to control a sensing unit or an actuating unit.
23. The system of any of items 7-22, wherein the core unit has an area equal to or less than 5 mm$^2$.
24. The system of any of items 7-23, wherein the core unit has a static power consumption equal to or substantially equal to zero when idle.
25. The system of any of items 1-24, wherein the communication interface of one or both of the implantable node and the gateway node comprises one or more ultrasonic transducers, and a transmitter chain and a receiver chain operative to transmit signals via the one or more ultrasonic transducers.
26. The system of any of item 25, wherein the transmitter chain and the receiver chain are coupled for ultrasonic transmission through biological tissue.
27. The system of any of items 25-26, wherein the receiver chain includes a low noise amplifier to amplify incoming signals and an analog-to digital converter to convert the incoming signals to digital signals.
28. The system of any of items 25-27, wherein the transmitter chain includes a power amplify to amplify outgoing signals and a digital-to-analog converter to convert the outgoing signals to analog signals.
29. The system of any of items 25-28, wherein the gateway node comprises an additional transmitter chain and an additional receiver chain for communication coupled for ultrasonic transmission through air with the access point node.
30. The system of any of items 25-29, wherein the one or more ultrasonic transducers comprise one or more of a piezoelectric transducer or an electrostatic transducer.
31. The system of any of items 25-30, wherein the one or more ultrasonic transducers comprises one or more micromachined ultrasonic transducers.
32. The system of any of items 1-31, wherein the communication interface further comprises a radio frequency transceiver to transmit and receive radio frequency communications.
33. The system of item 32, wherein the radio frequency transceiver is operative to transmit and receive radio frequencies wirelessly over short ranges.
34. The system of any of items 32-33, wherein the radio frequency transceiver is operative in one or both of the industrial, scientific and medical (ISM) radio band or the medical implant communication service (MICS) band.
35. The system of any of items 1-34, wherein the implantable node comprises an interface for attaching the sensing unit or the actuating unit.
36. The system of item 35, wherein the sensing unit or the actuating unit is detachably attachable to the interface.
37. The system of item 35, wherein the interface comprises an interface circuit board including a plurality of pin headers, and the sensing unit or the actuating unit includes a daughter board connectable to the pin headers of the interface circuit board.
38. The system of any of items 1-37, wherein the gateway node further comprises a sensing unit, an actuating unit, or an interface for a sensing unit or an actuating unit.
39. The system of any of items 1-38, wherein the gateway node includes an interface for a sensing unit or an actuating unit, the interface comprising an interface circuit board including a plurality of pin headers, and the sensing unit or the actuating unit includes a daughter board connectable to the pin headers of the interface circuit board.
40. The system of any of items 1-40, wherein the sensing unit of one or both of the implantable node and the gateway node comprises a sensor operative to sense a biological parameter.
41. The system of item 40, wherein the sensing unit is selected from the group consisting of a motion sensor, a gyroscope, an accelerometer, a cardiac rhythm monitor, a heart rate monitor, a pulse monitor, a blood pressure sensor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, and a sensor for pH, ionic strength or osmolality.
42. The system of item 41, wherein the sensor for one or more biomolecules comprises a sensor for one or more peptides, oligopeptides, polypeptides, proteins, glycoproteins, antibodies, antigens, nucleic acids, nucleotides, oligonucleotides, polynucleotides, sugars, disaccharides, trisaccharides, oligosaccharides, polysaccharides, lipids, glycolipids, proteolipids, cytokines, hormones, neurotransmitters, metabolites, glycosaminoglycans, and proteoglycans.
43. The system of any of items 1-42, wherein the actuating unit of one or both of the implantable node and the gateway node comprises an actuator operative to actuate a biological procedure.
44. The system of item 43, wherein the actuating unit of one or both of the implantable node and the gateway node is selected from the group consisting of a drug pump, a heart stimulator, a heart pacemaker, a bone growth stimulator, a deep brain stimulator, a neurostimulator, and a neuromuscular electrical stimulator.
45. The system of any of items 1-44, wherein the implantable node is implanted in the body.
46. The system of any of items 1-45, wherein the gateway node is worn on the body.
47. The system of any of items 1-46, wherein of one or both of the implantable node and the gateway node further include a power unit.

48. The system of item 47, wherein the power unit operates at a nominal voltage of at least 1.5 V.

49. The system of any of items 47-48, wherein the power unit comprises a battery.

50. The system of item 49, further comprising a charge pump circuit operative to store energy to generate a higher voltage power source in addition to the battery.

51. The system of any of items 49-50, further comprising a wireless energy transfer unit operative to utilize ultrasonic power transmission to charge the battery.

52. The system of any of items 47-51, wherein the power unit further comprises a human energy harvesting unit operative to harvest vibrational energy from heartbeats or voice reverberations, the human energy harvesting unit comprising an ultrasonic transducer.

53. The system of any of items 1-52, wherein the access point node is disposed on a computing device that includes an Internet connection.

54. The system of item 53, wherein the computing device comprises a smart phone, a tablet, a laptop, a desktop computer, a personal computer, a smart watch, smart glasses, or smart clothing.

55. The system of any of items 53-54, wherein the computing device includes a wired or a wireless connection to the Internet.

56. The system of any of items 1-55, wherein the access point node is disposed in air within a range of the gateway node sufficient to receive an ultrasonic communication or a radio frequency wireless communication from the gateway node 57. The system of any of items 1-56, where the access point node comprises one or both of an ultrasonic transceiver to transmit and receive ultrasonic communications and a radio frequency transceiver to transmit and receive radio frequency communications.

58. The system of any of items 1-57, wherein the access point node comprises an ultrasonic transceiver to transmit and receive in-air ultrasonic communications.

59. The system of any of items 1-58, wherein the access point node is operative to receive signals from one or both of the gateway node and the implantable node and to transmit the received signals to a further external device connected to the Internet.

60. The system of item 59, wherein the further external device comprises a computing device, a server, or a storage device.

61. The system of any of items 1-60, wherein the access point node is operative to receive instructions from a further external device connected to the Internet and to transmit the received instructions to one or both of the gateway node and the implantable node.

62. The system of any of items 1-61, wherein the implantable node is configurable or actuatable by instructions received at the access point node from a remote device over the Internet.

63. The system of any of items 1-62, wherein the network of implantable and wearable biological devices comprises a plurality of implantable nodes that are implantable in the body, each of the implantable nodes comprising a sensing unit or an actuating unit, an ultrasonic communication interface operative to transmit and receive ultrasonic signals through biological tissue, and a core unit in communication with the communication interface and with the sensing unit or actuating unit.

64. The system of any of items 1-63, wherein the network of implantable and wearable biological devices comprises a plurality of gateway nodes wearable on the body, each of the gateway nodes comprising a sensing unit or an actuating unit, an ultrasonic communication interface operative to transmit and receive ultrasonic signals through biological tissue, and a core unit in communication with the communication interface and with the sensing unit or actuating unit.

65. A system for transmitting signals ultrasonically through biological tissue comprising:
a network comprising a plurality of nodes, at least a first portion of the nodes implantable within a body, and at least a second portion of the nodes wearable on the body, each of the nodes operable to sense a biological parameter via a sensing unit or to actuate a biological procedure via an actuating unit; and
at least one of the implantable nodes or at least one of the wearable nodes comprising a configurable node, the configurable node comprising:
a sensing/actuating interface for a sensing unit or an actuating unit,
an ultrasonic communication interface operative to transmit and receive ultrasonic signals transmitted through biological tissue, and
a core unit in communication with the sensing unit and the ultrasonic communication interface, the core unit comprising a processor and memory operative to receive instructions to configure the configurable node for a sensing unit or actuating unit connected at the sensing/actuating interface.

66. The system of item 65, wherein the processor comprises at least a microcontroller and a programmable logic device operative to execute communication, processing and networking tasks.

67. The system of item 66, wherein the microcontroller unit is operative at upper layers of a protocol stack to enable ultrasonic communication.

68. The system of any of items 66-67, wherein the microcontroller unit is operative at one or more of a data link layer, a network layer, a transport layer, and an application layer of a protocol stack to enable ultrasonic communication.

69. The system of any of items 66-68, wherein the programmable logic device comprises a field programmable gate array (FPGA).

70. The system of item 69, wherein the core unit includes one or both of a serial peripheral interface (SPI) and an inter integrated circuit (I2C) interface to control communications between the microcontroller, the FPGA, the communications interface, the sensing unit or actuating unit, and memory.

71. The system of any of items 69-70, wherein the FPGA is operative at a physical layer of a protocol stack to enable ultrasonic communication.

72. The system of any of items 69-71, wherein the FPGA is programmable to control a sensing unit, the sensing unit selected from the group consisting of a motion sensor, a gyroscope, an accelerometer, a cardiac rhythm monitor, a heart rate monitor, a pulse monitor, a blood pressure sensor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, and a sensor for pH, ionic strength or osmolality.

73. The system of item 72, wherein the sensor for one or more biomolecules comprises a sensor for one or more peptides, oligopeptides, polypeptides, proteins, glycoproteins, antibodies, antigens, nucleic acids, nucleotides, oligonucleotides, polynucleotides, sugars, disaccharides, trisaccharides, oligosaccharides, polysaccharides, lipids, glycolipids, proteolipids, cytokines, hormones, neurotransmitters, metabolites, glycosaminoglycans, and proteoglycans.

74. The system of any of items 69-73, wherein the FPGA is programmable to control an actuating unit, the actuating unit selected from the group consisting of a drug pump, a heart stimulator, a heart pacemaker, a bone growth stimulator, a deep brain stimulator, a neurostimulator, and a neuromuscular electrical stimulator.

75. The system of any of items 65-74, wherein the sensing/actuating interface comprises an interface circuit board including a plurality of pin headers connectable to a daughter board of a sensing unit or an actuating unit.

76. The system of item 75, further comprising a sensing unit or an actuating unit detachably attached to the interface.

77. The system of any of items 65-76, wherein the configurable node further includes a power unit.

78. A method for transmitting signals ultrasonically among a network of implantable and wearable biological devices, comprising:
providing at least one implantable node, implanted in a body, a gateway node wearable on the body, and an access point node in air, each of the nodes comprising an ultrasonic communication interface operative to transmit and receive ultrasonic signals through biological tissue or in air, at least the implantable node further including a sensing unit or an actuating unit; and
transmitting ultrasonic signals between the implantable node and the gateway node or between the implantable node and the access point node.

79. The method of item 78, further comprising ultrasonically transmitting instructions from the gateway node to the implantable node to configure the sensing unit to sense a desired biological parameter or to configure the actuating unit to actuate a desired biological procedure, wherein the instructions comprise instructions to program a programmable logic device at the implantable node.

80. The method of item 79, wherein the instructions to the implantable node are received by the access point node from a remote device, and the access point node transmits the instructions to the gateway node.

81. The method of item 80, wherein the instructions are received by the access point node from a transmission from a remote device connected to the Internet.

82. The method of any of items 78-81, further comprising ultrasonically transmitting instructions from the access point node to the implantable node to configure the sensing unit to sense a desired biological parameter or to configure the actuating unit to actuate a desired biological procedure, wherein the instructions comprise instructions to program a programmable logic device at the implantable node.

83. The method of item 82, wherein the instructions are received by the access point node from a transmission from a remote device connected to the Internet.

84. The method of any of items 78-83, further comprising transmitting data obtained by a sensing unit at the implantable node ultrasonically to the gateway node.

85. The method of item 84, further comprising transmitting the data from the gateway node ultrasonically to the access point node.

86. The method of item 85, further comprising transmitting the data from the access point node to a remote device.

87. The method of any of items 85-86, further comprising transmitting the data from the access point node to a remote device over the Internet.

88. The method of any of items 86-87, wherein the remote device comprises a computing device, a service, or a storage device.

89. The method of any of items 78-88, further comprising receiving instructions at the access point node to actuate the actuating unit from a remote device.

90. The method of item 89, further comprising receiving the instructions from a remote device over the Internet.

91. The method of any of items 78-90, further comprising transmitting radio frequency signals between the gateway node and the access point node.

92. The system of any of items 78-91, further comprising transmitting instructions from the access point node to the gateway node, and transmitting the instructions from the gateway node to the implantable node.

93. The system of any of items 78-92, further comprising transmitting data obtained by a sensing unit at the implantable node to a further implantable node, implanted in the body and comprising an actuating unit to actuate the actuating unit in response to the obtained data.

DESCRIPTION OF THE DRAWINGS

The invention will be more fully understood from the following detailed description taken in conjunction with the accompanying drawings in which.

DETAILED DESCRIPTION OF THE INVENTION

Figure 1:
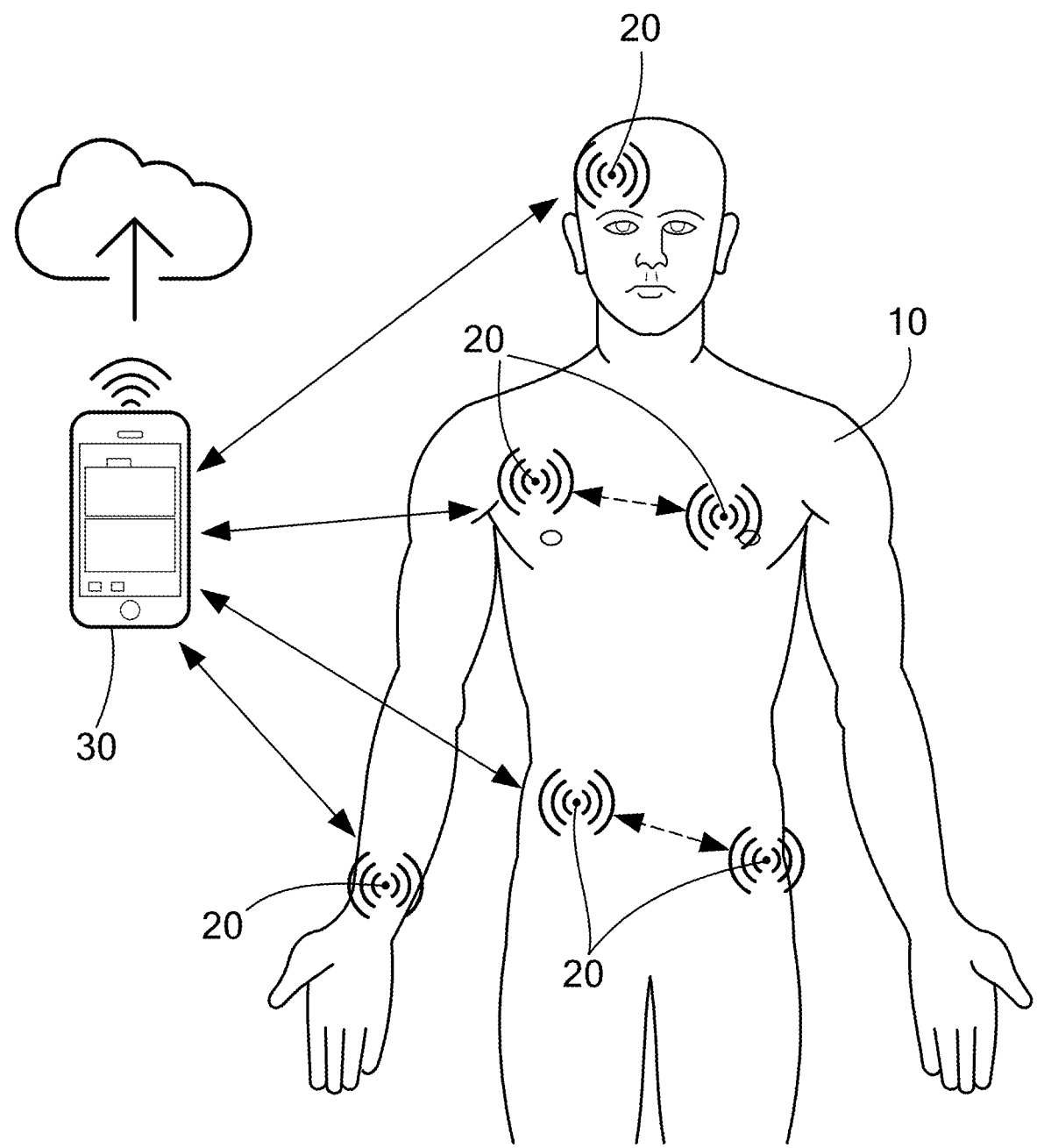
FIG. 1 is a schematic illustration of an ultrasonic communication system for transmitting data ultrasonically among wearable devices.

A ultrasonic communication system and method are provided to interconnect a network of intra-body implantable devices and wearable devices, provide an Internet of Medical Things (IoMT) capability, and enhance the configurability of the devices.

An Internet of Medical Things (IoMT) platform allows the remote measurement, storage and management on the cloud of biological parameters of a patient measured by implantable sensors, as well as remote control of actuating devices deployed in the body of the patient, e.g., stimulators, injecting and pacing devices, and enabling of closed-loop feedback applications. Through telemetry, the platform can allow measuring, storing, and delivering out-the-body vital biological parameters of the patient as measured by a variety of implantable sensors; it can also enable remote control from outside the body of actuation devices implanted in the body of the patient, including stimulators, pacers, and drug pumps. Furthermore, the ultrasonic IoMT platform can also support implant-to-implant interaction through entirely intra-body communication links. This can enable closed-loop applications in which an actuator performs an action (e.g., a stimulation) based on physiological data captured by sensors implanted elsewhere in the body.

In some embodiments, the system can include an intra-body network of a plurality of nodes implantable in a body. Each node comprises an implantable device including one or more sensors and/or one or more actuators. The implantable nodes can communicate through ultrasound with one or more gateway nodes, each comprising an ultrasonic device, deployed along the body of the patient. The gateway nodes enable communication from the intra-body network to access point nodes, each comprising an ultrasonic device, through ultrasound or through radio frequency-based technologies. The access point device connects the system to an external network, such as the Internet, enabling, for example, remote monitoring of the gateway and implantable nodes, control of the gateway and implantable nodes, and cloud storage of data on a remote server. The implantable nodes can also communicate directly to the access point nodes when needed.

1. Ultrasonic Communication System for Implantable and Wearable Devices

As noted above, the communication system employs ultrasonic transmissions for communication between implantable and wearable devices in place of or, in some embodiments, accompanied by radio frequency transmission. Radio frequency technology presents a number of limitations when adapted to implantable and wearable devices. First, the RF frequency spectrum is scarce, strictly regulated, and already crowded with many devices interfering with one another. Therefore, RF-based technologies raise serious concerns about potential interference from existing RF communication systems that can unintentionally undermine the reliability and security of a wearable network, and ultimately the safety of the patient. Also, RF communications can be easily jammed, i.e., intentionally disrupted by artificially generated interference, or eavesdropped by malicious agents. This raises major privacy and security concerns for wearable networks, and a risk for the patient. Additionally, the medical community is still divided on the risks caused by continuous exposure of human tissues to RF radiation. Therefore, a massive deployment of RF wearable devices on the body may represent a potential risk for the patient. Further, the dielectric nature of the human body also affects the coupling between on-body RF antennas and the body itself. In particular, the gain and the radiation pattern of the antenna deteriorate because of the contact or proximity with the human body while the resonant frequency and the input impedance of the antenna may shift from their nominal values.

The present system and method employ ultrasonic waves, which are acoustic waves with frequency higher than the upper threshold for human hearing (nominally 20 kHz). The present ultrasonic communication system has several advantages over traditional networking frameworks based on RF communications. The system eliminates any potential conflict with existing RF communication systems and over-crowded RF environments. The ultrasonic frequency spectrum is currently unregulated, giving high flexibility to the system in terms of ultrasonic spectrum allocation. The system enables nodes to flexibly adapt the occupied frequency to specific requirements, such a maximum level of tolerable co-channel interference, maximum tolerable channel multipath and Doppler spreading in the channel and minimum data rate needed at the application layer. As compared to RF waves, ultrasonic waves do not easily penetrate in solid materials and do not propagate far in air; therefore, the ultrasonic communication system is inherently more secure with respect to eavesdropping and jamming attacks, which require close proximity. The medical experience of the last decades has demonstrated that ultrasounds are fundamentally safe, as long as acoustic power dissipation in tissues is limited to predefined safety levels. By equipping wearable devices with ultrasonic transducers, the present system can also implement ultrasonic power transmission schemes that enable wireless battery charging functionalities. On-board ultrasonic transducers can also be used to enable acoustic localization and tracking functionalities, which have better accuracy than RF-based systems because of the low propagation speed of sound in air. The low-propagation speed of sound also eases detection in the presence of strong multipath with respect to RF waves, because of the higher difference in propagation time between multiple paths. The system can be interfaced with ultrasonic intra-body networks, and can work as a bridge between intra-body sensors and the external world. The software-defined framework can run on general-purpose hardware; thus, it can enable commercial devices, such as smartphones, laptops and smart-TVs, to communicate with ultrasonic wearable devices in the near-ultrasonic frequency range, i.e., from 15 or 17 kHz to 20 or 22 kHz, using commercial-off-the-shelf (COTS) speakers and microphones. The software-defined ultrasonic networking functionalities can be reconfigured to adapt to application requirements, offering more flexibility with respect to traditional RF-based networking systems entirely implemented in hardware, e.g., Bluetooth or Wi-Fi.

The system includes a set of software-defined cross-layer functionalities tailored for networking ultrasonic wearable devices that offer real-time reconfigurability at different layers of the protocol stack, i.e., the physical (PHY), data link, network and application layer. More specifically, the system encloses a set of PHY, data link and network functionalities that can flexibly adapt to the application and system requirements, to optimally network information between ultrasonic wearable devices. The system also offers real-time reconfiguration at the application layer to provide a flexible platform to develop medical applications. In particular, the system includes sensor data processing applications running in nodes of a network that can be decomposed into primitive building blocks that can be arbitrarily arranged to create new sensing applications to fit the user requirements.

Embodiments of the system and method employ aspects at different layers of the protocol stack to overcome limitations posed by the propagation characteristics of ultrasonic waves in air. For example, two signaling schemes (GMSK and orthogonal frequency-division multiplexing (OFDM), discussed further below) can be suitably used because of their high spectral efficiency and resilience to multipath. Two different synchronization modes can be alternatively and suitably used for channels strongly affected by multipath or by Doppler effect. Upper layer protocols and functionalities can be selected to address challenges posed by the long propagation delays of ultrasounds in air that might prevent accurate timing.

2. Ultrasonic Intra-Body and Airborne Communications

Ultrasounds are mechanical pressure waves that propagate through elastic media at frequencies above the upper limit for human hearing, i.e., 20 kHz.

Attenuation. Two main mechanisms contribute to ultrasound attenuation in tissues, i.e., absorption and scattering. An initial pressure $P_0$ decays at a distance d $$P(d) = P_0 e^{-\alpha d}$$

where $\alpha$ (in $[Np \cdot cm^{-1}]$) is an amplitude attenuation coefficient that captures all the effects that cause dissipation of energy from the ultrasound wave. Parameter $\alpha$ depends on the carrier frequency through $\alpha = a f^b$, where f represents the carrier frequency (in MHz) and a (in $[Np\ m^{-1}\ MHz^{-b}]$) and b are attenuation parameters characterizing the tissue.

Two mechanisms mainly contribute to acoustic attenuation in air, i.e., spreading loss and absorption loss. The former includes spherical spreading, i.e., the acoustic pressure falls off proportionally to the surface area of a sphere. The latter is mainly related to atmospheric absorption caused by the interaction of the acoustic wave with the gas molecules of the atmosphere and is frequency, temperature, and humidity dependent.

For a signal at frequency f [Hz] over a transmission distance d [m], the attenuation can be expressed in [dB] as $$A_{dB} = 20\ \log_{10}(d) + d\alpha(f),$$

where $\alpha(f)$ [dB/m] is the absorption coefficient, which increases quadratically with the frequency, but also depends on the ambient atmospheric pressure, temperature, and the molar concentration or water vapor, i.e., humidity.

Propagation Speed. Ultrasonic wave propagation is affected by propagation delays that are orders of magnitude higher than RF. The propagation speed of acoustic waves in biological tissues is approximately 1500 m/s, as compared to $2 \times 10^8$ m/s for RF waves.

The propagation speed of acoustic waves in air is approximately 343 m/s at a temperature of 20° C. and at atmospheric pressure of 101.325 kPa, as compared to $3 \times 10^8$ m/s for RF electromagnetic waves. The speed of sound in air increases with temperature and humidity, going from 331 m/s at a temperature of 0° C. and 10% relative humidity to 351 m/s at a temperature of 30° C. and 90% relative humidity.

Operating Frequency. Considerations in determining the operating frequency are (i) the frequency dependence of the attenuation coefficient, and (ii) the frequency dependence of the beam spread of ultrasonic transducers (which is inversely proportional to the ratio of the diameter of the radiating surface and the wavelength). Therefore, higher frequencies help keep the transducer size small, but result in higher signal attenuation. Since most biomedical sensing applications require directional transducers, one needs to operate at the lowest possible frequencies compatible with small-size transducers and required signal bandwidth. For propagation distances in the order of several cm. the operating frequency should not exceed 10 MHz.

Doppler Spreading. Doppler spreading occurs as a result of Doppler shifts caused by relative motion between source and receiver, and is proportional to their relative velocity. Doppler spreading generates two different effects on signals: a simple frequency translation, and a continuous spreading of frequencies that generates intersymbol interference (ISI), thus causing degradation in the communication performance. Since the speed of sound is several orders of magnitude lower than the speed of electromagnetic waves, the resulting Doppler effect is severe, even at relatively low speeds.

Reflections and Scattering. The human body is composed of different organs and tissues with different sizes, densities and sound speeds. Therefore, it can be modeled as an environment with pervasive presence of reflectors and scatterers. The direction and magnitude of the reflected wave depend on the orientation of the boundary surface and on the acoustic impedance of the tissues, while scattered reflections occur when an acoustic wave encounters an object that is relatively small with respect to its wavelength or a tissue with an irregular surface. Consequently, the received signal is obtained as the sum of numerous attenuated, possibly distorted, and delayed versions of the transmitted signal.

The on-body ultrasonic channel is composed of several interfaces between air and human body, and between air and on-body and near-body objects. Because of this inhomogeneous pattern, the on-body channel can be modeled as an environment with pervasive presence of reflectors and scatterers. The direction and magnitude of the reflected wave depend on the orientation of the boundary surface and on the acoustic impedance of the different media involved. Scattered reflections occur when an acoustic wave encounters an object that is relatively small with respect to its wavelength. (The acoustic impedance is defined as the product between the density of a medium p and the speed of sound in the medium c.) Consequently, the received signal is obtained as the sum of numerous attenuated, possibly distorted, and delayed versions of the transmitted signal.

Ultrasonic Transducers. An ultrasonic transducer is a device that converts electrical signals into ultrasonic signals and vice versa. Ultrasonic transducers can be categorized into two main classes based on the physical mechanism that enables the conversion, i.e., piezoelectric and electrostatic transducers. A piezoelectric transducer produces a mechanical vibration through a thin piezoelectric element under an external voltage variation, and produces a voltage variation under an external mechanical vibration. In electrostatic transducers the fundamental mechanism is the vibration of a thin plate under electrostatic forces.

When sound passes across an interface between two materials, it is in part transmitted and in part reflected. To maximize the acoustic energy radiated by the transducer, the acoustic impedance of the radiating surface should match the acoustic impedance of the propagation medium. Today, microelectro-mechanical (MEMS) technology has enabled the fabrication of microscopic piezoelectric and electrostatic transducers, i.e., so-called Micromachined Ultrasonic Transducers (MUTs). With MUTs, the acoustic impedance can be controlled to match the external medium by manipulating the device geometry. This characteristic makes MUTs suitable for air-coupled applications.

When the operating frequency of the ultrasonic communications falls in the near-ultrasonic frequency range, i.e., 15 to 17 kHz to 20 to 22 kHz, acoustic waves can be recorded and generated using components, such as microphones and speakers, which can be commercial off the shelf (COTS) components. Even though COTS components are often designed to operate a lower frequencies, i.e., at 0-17 kHz, they can still sense and generate, albeit less efficiently, near-ultrasonic frequency waves. Since many commercial devices such as smartphones, tablets and laptops among others, are equipped with audio interfaces, they can in some embodiments, support near-ultrasonic communications with no additional hardware.

3. System Architecture

The system comprises a set of software-defined multilayer functionalities that can be implemented on general-purpose processing units, e.g., microprocessors, microcontrollers or FPGAs, among others, to enable networking operations between wearable devices equipped with airborne ultrasonic connectivity, i.e., air-coupled ultrasonic transducers, and sensing capabilities, i.e., sensors.

Figure 2:
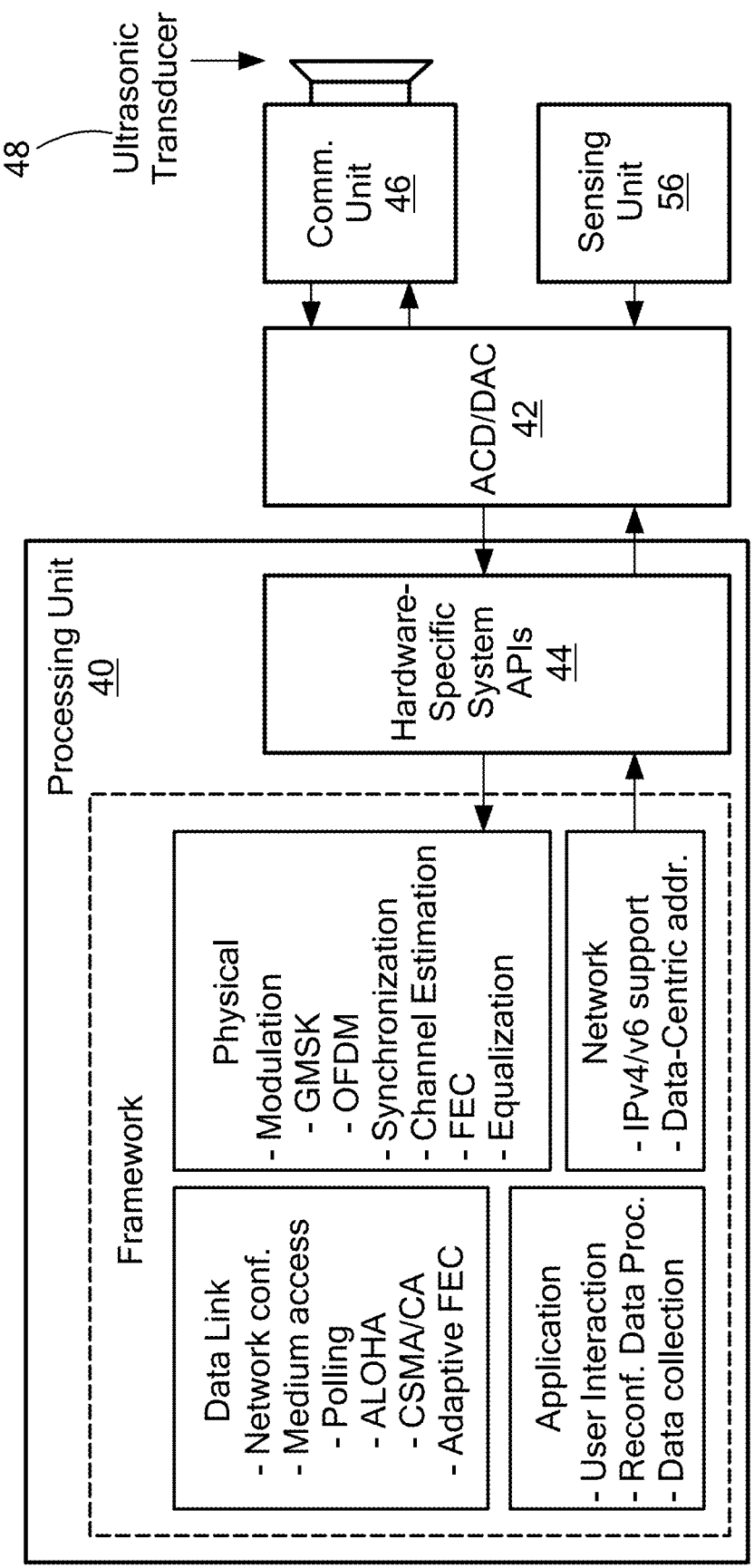
FIG. 2 is a schematic block diagram of a networking framework of the ultrasonic communication system.
Figure 3:
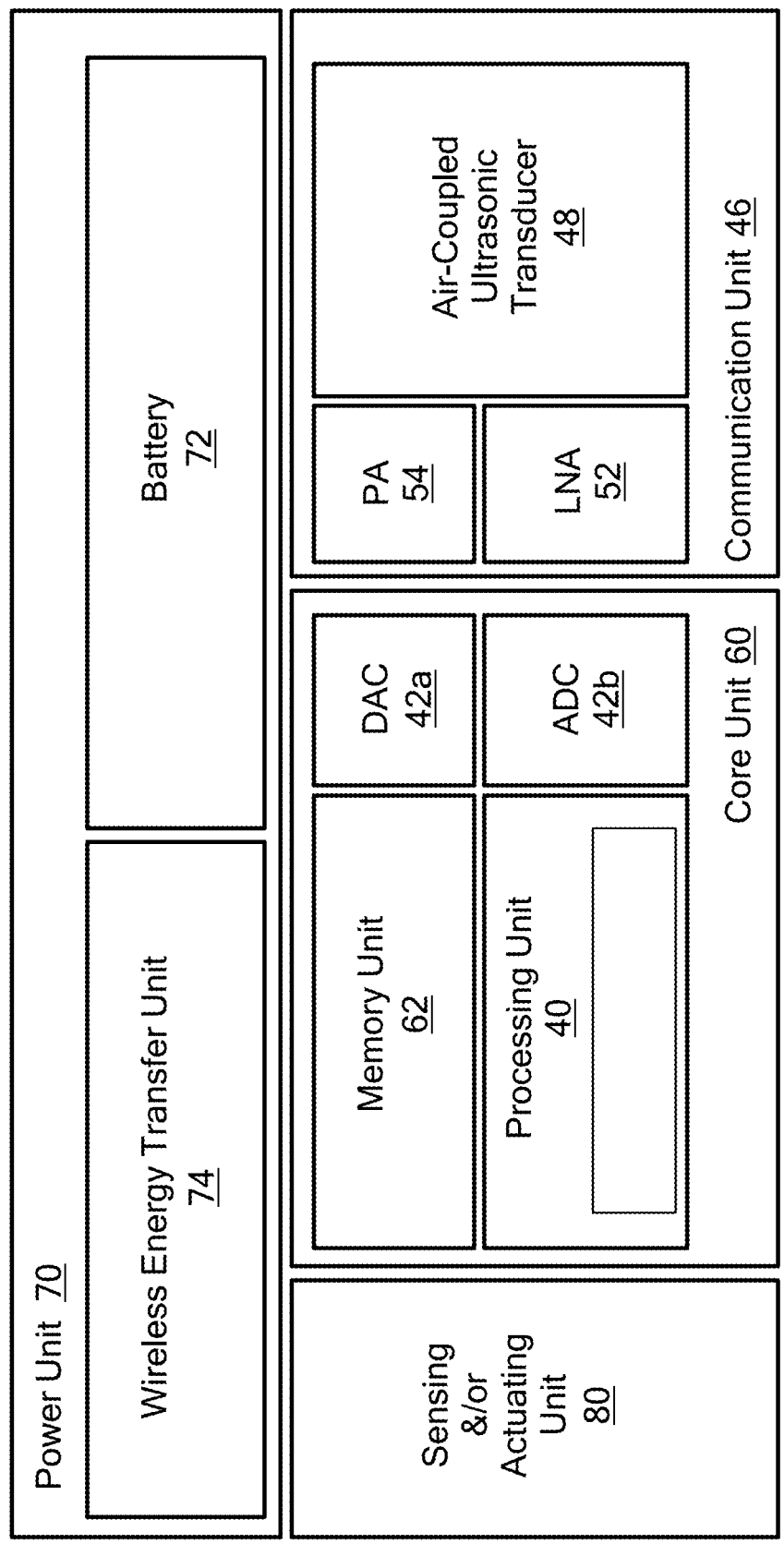
FIG. 3 is a schematic block diagram of a hardware embodiment of the ultrasonic communication system.

FIG. 2 shows an embodiment of an overview of the framework architecture, and FIG. 3 shows an embodiment of the hardware architecture. The system runs on a processing unit 40, which can access a hardware analog-to-digital converter (ADC) and digital-to-analog converter (DAC) 42 through hardware-specific system application programming interfaces (APIs) 44. In the transmission (Tx) chain, the DAC 42a collects and digital-to-analog converts the digital outputs, i.e., the waveforms to be transmitted generated by the processing unit, before passing these to a communication unit 46. In the receiving (Rx) chain, the ADC 42b analog-to-digital converts and passes to the processing unit the received waveforms coming from the communication unit 46. The communication unit includes an ultrasonic transceiver, for example, an ultrasonic transducer 48 and an amplification stage, i.e., a preamplifier 52 in the Rx chain and a power amplifier 54 in the Tx chain. The processing unit also collects the analog-to-digital converted data coming from a sensing unit 56. The communication framework at the processing unit comprises (i) physical (PHY) layer functionalities, e.g., modulation and synchronization, (ii) data link layer functionalities including forward error control or medium access control (MAC) protocols, (iii) network layer functionalities, e.g., IPv4 and IPv6 support and content-centric networking, and (iv) application layer functionalities, i.e., reconfigurable sensing data processing and user interface.

3.1 Physical Layer

The communication framework PHY layer defines the signaling scheme, channel estimation, equalization, synchronization and forward error correction (FEC) functionalities.

3.1.1 Signaling Schemes

In some embodiments, the framework can employ two fully-functional signaling schemes, a narrowband scheme based on Gaussian minimum-shift keying (GMSK) modulation, and a wideband scheme based on orthogonal frequency-division multiplexing (OFDM). Moreover, the framework includes a set of software-defined primitive blocks, e.g., programmable filters, and Fast Fourier Transform (FFT) modules, among others, that can be used to implement additional signaling schemes.

Narrowband GMSK. GMSK is a continuous-phase modulation (CPM) used in GSM cellular systems. In frequency-shift keying (FSK) and phase-shift keying (PSK) the information is encoded in the variations of the carrier frequency or carrier phase, respectively. Since frequency and phase switches occur instantaneously, FSK and PSK signals do not have continuous phase. Phase discontinuity generates out-of-band power, leading to poor spectral efficiency. Moreover, in near-ultrasonic transmissions based on COTS speakers and microphones, the out-of-band power introduces audible noise (clicks), which make the communication perceptible to humans.

GMSK signals have instead phase continuity, and each symbol is represented by a phase variation, from the starting value to a final value, over the symbol duration, i.e., phase trajectory. Thus, the initial phase of each symbol is determined by the cumulative total phase variation of all previous symbols, i.e., there is phase memory. A Gaussian filter is used to smooth the phase trajectory and improve the spectral efficiency. The product between the signal bandwidth B and the symbol time T is a measure of the scheme spectral efficiency. A lower BT product leads to higher spectral efficiency, but increases the intersymbol interference (ISI). Based on these characteristics, GMSK is a suitable signaling scheme for the narrowband communications in the near-ultrasonic frequency range, which may use, for example, COTS speakers and microphones. Due to its phase-continuity, GMSK enables click-free transmissions, which can be advantageous over non-continuous-phase modulations such as frequency shift keying (FSK) and phase shift keying (PSK).

Wideband OFDM. OFDM provides robustness against frequency selective channels with long delay spreads. The principle of OFDM is to use a large number of closely spaced orthogonal sub-carriers, such that for each sub-carrier the channel is subject to flat fading. In each sub-carrier a conventional modulation scheme can be used, such as M-PSK and M-Quadrature-Amplitude-Modulation (QAM). OFDM offers high spectral efficiency and robustness against narrowband co-channel interference, intersymbol interference (ISI) and multipath fading effect. OFDM can be efficiently implemented using FFT and inverse FFT (IFFT) algorithms. These characteristics make OFDM suitable for ultrasonic communications based on wideband transducers.

3.1.2 Synchronization

Synchronization in the communications framework can be achieved in two steps. First, an energy collection approach identifies any incoming packet, i.e., coarse synchronization. Once a packet is detected, the receiver performs a fine synchronization operation that identifies the exact starting point of the packet. Fine synchronization is achieved by correlating the received signal with a local copy of the preamble, i.e., a sequence that precedes each packet, which outputs a peak corresponding to the first sample of the packet.

Two synchronization modes can suitably be used in the present communications framework:

PN-sequence mode. The pseudo noise (PN)-sequence mode uses PN-sequences as a preamble, i.e., binary sequences with sharp autocorrelation peak and low cross-correlation peaks, that can be deterministically generated. In one embodiment, maximum length sequences (MLSs), a particular family of PN-sequences are used. MLSs can be generated in software and hardware through linear feedback shift registers (LFSRs). Because of the desirable correlation characteristics, PN-sequences are suitable for enabling strong resilience to multipath, as in ultrasonic in-body and in-air communications.

Chirp-based mode. The chirp-based mode uses a chirp signal as preamble, i.e., a sinusoidal waveform whose frequency varies from an initial frequency $f_0$ to a final frequency $f_1$ within a certain time T. Chirp signals provide good auto-correlation and robustness against Doppler effect. A frequency-shifted chirp can correlate well with the original chirp, although with lower amplitude and time-shifted peak. This characteristic makes chirp synchronization desirable for ultrasonic in-air communications under severe Doppler effect conditions, for example, fast moving sensor nodes worn by athletes for performance monitoring. The price for the Doppler robustness is higher cross-correlation peaks compared to PN-sequences that result in lower resilience to multipath effect.

3.1.3 Channel Estimation and Equalization

As discussed above, ultrasonic in-air communications are strongly affected by multipath and Doppler spread, leading to frequency selectivity and inter-symbol interference (ISI) that compromise the bit recovery operations at the receiver. The present framework implements channel estimation and equalization functionalities to estimate the channel impulse response (CIR) and mitigate the distortion produced by the channel.

Channel Estimation. The communication system can utilize a training-based channel estimation approach that requires the presence of a training sequence known a priori in the transmitted packet. In particular, the system leverages the good-autocorrelation property of the synchronization preamble sequence, discussed in Section 2.1.2 above, to estimate the CIR. By correlating the output of the channel, i.e., the received signal, with the input, i.e., the known preamble sequence, an estimate of the time-domain CIR can be obtained.

Zero-forcing Equalization. The system can implement a linear equalization technique, zero-forcing (ZF) equalization, that aims to minimize the ISI signal distortion produced by the channel. A ZF equalizer is a finite-impulse-response (FIR) filter of order N that, for each input symbol, forces to zero the ISI components introduced by the 2N adjacent symbols. The filter taps are numerically calculated starting from an estimate of the CIR, which also accounts for the ISI effect.

3.1.4 Forward Error Correction

The system can include a forward error correction (FEC) functionality, based in some embodiments on Reed-Solomon (RS) codes. RS codes are linear, block error-correcting codes used in data storage and data transmission systems. A RS encoder takes k information symbols and adds t parity symbols to make an n symbol block. Therefore, there are t=n−k overhead symbols. On the other hand, a RS decoder is able to decode the received n-symbol block, and can correct up to t/2 data symbols that may contain potential errors due to the channel fluctuation or collisions with interfering packets. The RS coding rate can be defined as the ratio between the message length and the block length, i.e., k/n.

3.2 Data Link Layer

The data link layer provides a set of functionalities that allow multiple nodes to efficiently access a shared medium, i.e., a network configuration, multiple access protocols and PHY layer adaptation, under the challenges posed by an ultrasonic in-body and in-air channel, such as long propagation delays, among others, as discussed in Section 2 above.

3.2.1 Network Configuration

The system can internetwork wearable devices in master/slave (M/S) or peer-to-peer (P2P) configurations. Both configurations can coexist in the same network in hybrid configurations. For example, referring to FIG. 1, a master/slave configuration is shown by solid lines between the nodes and a peer-to-peer configuration is shown by dashed lines.

Master-Slave Configuration. In the M/S configuration, one node takes the role of master, i.e., network coordinator, while the remaining nodes operate as slaves. In this scenario, the network control is concentrated on a master node, typically with higher resources available, e.g., processing, memory, power and connectivity. For example, an M/S configuration may be used in continuous monitoring systems where a master processing node 30, e.g., a smartphone, or a laptop, is used to fetch, analyze and display data collected by wearable sensors at nodes 20. Wireless or wired Internet connectivity can allow the master node to connect the wearable network with, for example, a medical center where a patient's data can be stored and analyzed remotely.

Peer-to-Peer Configuration. In the P2P configuration, all the network wearable nodes 20 are treated as peers. This scenario suits, among others, applications that require distributed coordination among nodes for closed-feedback-loop monitoring and actuating tasks. For example, this may include a skin patch drug-delivery system where a drug pump can trigger a sensor for measurement, as well as where a sensor may trigger the drug pump for drug injection after a measurement.

3.2.2 Medium Access Control Protocols

The system can employ fully-functional multiple access protocols, such as, for example, polling, ALOHA and carrier sense multiple access (CSMA) with collision avoidance (CA), as well as primitive functions to implement custom protocols, e.g., idle listening, random backoff, or checksum-based error control mechanism.

Polling Protocol. Polling is a deterministic access protocol for an M/S network configuration. In a polling scheme, the master node has complete control over channel access, while each slave node is granted access to the medium in a round-robin fashion.

ALOHA. ALOHA is a random access protocol where nodes do not check whether the channel is busy or idle before transmitting. Nodes that want to transmit data simply access the channel and transmit the data. When collisions occur, nodes attempt retransmissions after a random time interval, i.e., backoff time.

Carrier Sense Multiple Access. CSMA/CA is a multiple access technique based on carrier detection, which allows multiple nodes to share the channel by avoiding simultaneous transmissions, therefore avoiding collisions among transmitted packets. When a node wants to transmit a data packet, it first listens to the channel. If the channel is sensed as idle during a fixed time interval, the node transmits, otherwise waits for a backoff time before attempting a new transmission.

In some embodiments, distributed medium access control coordination can be achieved by exchanging information on logical control channels, while data packets are transmitted over logical data channels. Unicast transmissions between a transmitter TX and a receiver RX are considered, as follows.

When TX needs to transmit a packet, it first needs to reserve a dedicated channel to RX. The connection is opened through the common control channel using a two-way handshake procedure. In some embodiments, using, for example, an OFDM modulation scheme, the control channel can be implemented using a fixed control channel and in some embodiments, a random control channel. In the fixed control channel approach, a fixed number of preassigned subcarriers are allocated to transmit and receive control information. In the control subcarriers the communication follows a unique time-hopping sequence known and shared by all network devices. All the nodes listen to the fixed control channel and wait for a request from a transmitting node. The control channel is accessed through a contention phase.

In the random control channel approach, control channel is implemented in a frequency-hopping fashion, i.e., the control channel subcarrier allocation changes pseudo-randomly in time. Synchronization between the transmitting and receiving nodes is possible by guaranteeing that the transmitter use all the channels in a fixed period of time, so that the receiver can then find the transmitter channel by picking a random channel and listening for valid data on that channel.

In the two-way handshake procedure, TX sends a Request-to-Transmit (R2T) packet to RX, which contains its own ID. If RX is idle, a Clear-to-Transmit (C2T) control packet is sent back to TX. In case of failure and consequent timer expiration, TX will attempt a new transmission after a random backoff time, for a maximum of $N_R$ times. After receiving the C2T packet, the transmitter switches to a dedicated channel by computing its own frequency- and time-hopping sequence by seeding a pseudo-random sequence generator with its own ID. As a consequence, both TX and RX leave the common channel and switch to a dedicated channel. The receiver RX computes the optimal transmission strategy, i.e., number of occupied subcarrier, time-hopping frame length, FEC coding rate and modulation. This information is piggybacked into ACK or NACK packets.

Once the communication has been established, RX does not leave the common control channel. Instead, it keeps "listening" to both the dedicated and common control channels at the same time. In the dedicated control channel, RX sends to TX the optimal strategy information to be used for the next transmission. In the common control channel, RX exchanges with other co-located receivers information on the level of tolerable interference.

3.2.3 PHY Layer Adaptation

The system defines a set of cross-layer functionalities that enable real-time reconfiguration of PHY layer parameters from upper layers of the protocol stack, e.g., data link or network layer. By leveraging the flexibility of the software-defined architecture, upper layer protocols can reconfigure on-the-fly PHY layer parameters such as modulation, signal bandwidth and FEC coding rate, among others. Reconfiguration functionalities allow development of reactive or proactive control algorithms to adapt the underlying communication link to the channel variations or to upper layer protocol requirements.

3.3 Network Layer 3.3.1 IPv4 and IPv6 Support

The system can provide interoperability with the Internet by defining an adaptation layer that integrates IPv4 and IPv6 protocol support. The adaptation layer comprises a set of functionalities that interface the traditional IP network layer with the data link layer, by offering IP header compression and IP packet fragmentation functions optimized for ultrasonic wearable networks with long propagation delays that potentially prevent accurate timing of network protocols. For example, by leveraging cross-layer header information, the long IPv4 and IPv6 headers can be shortened to reduce network delay and energy consumption when exchanging small information packets.

3.3.2 Content-Centric Networking

The system can provide content-centric networking (CCN) functionalities that make the network content directly addressable and routable. Each sensor data or actuation command, i.e., each content object, is labeled with a name, and can be accessed through this name. Nodes can request content objects by broadcasting a request message. When a match is found, i.e., the content is found on a network node, a response message containing the requested content is sent back.

3.4 Application Layer 3.4.1 Reconfigurable and Modular Data Processing

The system adopts the idea of decomposing the data processing applications running in the sensor nodes into primitive blocks, and can offer real-time reconfigurability at the application layer. The sensing application comprises a sequence of basic operations that are executed on the sensor data to extract desired medical parameters. Real-time modular reconfiguration offers three main advantages. First, the network coordinator can wirelessly install new applications on sensor nodes at runtime, as needed. Based on this, resources are allocated only when the application is requested, thus reducing the processing and memory overhead due to static applications continuously running in background. Second, modular reconfiguration enables programmers to easily create new applications by arranging the primitive building blocks in the desired execution sequence. As a consequence, new medical parameters can be extracted from the raw data coming from a sensor, while maximizing code reusability. Finally, in case of template matching applications, e.g., ECG anomaly detection by matching ECG traces with known templates, adding or updating templates becomes simple with a reconfigurable application layer.

Defining new applications comprises specifying inputs, a chain of primitive blocks, and outputs. An input is the physical sensor that generates the data, e.g., accelerometer or electrocardiogram (ECG). An output can be either the local memory for storing a measured parameter, or a transmission for sending a measured parameter to another node. Outputs can be associated with triggering events, e.g., transmit a packet or store a measure if its value falls in a given range, or can be periodic. For each application, a sampling rate, i.e., how often to sample the input sensor data, and a sampling interval, i.e., how long to process the data for, is defined. The set of primitive blocks is divided into three main classes, filters, data operations, and detectors. Filters enable filtering the raw data to remove offsets, drift of the sensors and any other noise components coming from external sources. Data operations include common signal processing operations performed on sensor data, e.g., correlation with templates, and FFT, among others. Detectors allow measuring the desired parameters by detecting specific elements in the processed signal, e.g., peaks, patterns and time distances, among others.

3.4.2 Data Collection

The application layer can operate in two different modalities to exchange and collect data: fetch mode and push mode.

Fetch Mode. Fetch mode is used when the application layer requires content from the network, and the node transmits a request mask to fetch this data. The node waits for a response from one or more nodes that possess the requested content. When a response is correctly received, if all the requested entities have been received the node goes back to the idle state.

Push Mode. Push mode is used when sensed data needs to be pushed to another node, e.g., high glucose level in the blood, or when a node requires another node to accomplish some actuating operation, e.g., inject insulin or trigger a neurostimulation. In case of actuating commands, the push packet can contain further information about the required action, e.g., the quantity of insulin to inject or the pattern of the neurostimulation.

4. Prototypes

Two prototypes have been built that implement the framework discussed in Section 2 above. The first prototype is a wearable ultrasonic sensor node based on a custom hardware platform, referred to as a wearable node. The second prototype is a wearable ultrasonic coordinator based on an iOS commercial smartphone device, referred to as a wearable master.

4.1 Wearable Node Prototype 4.1.1 Hardware Design

FIG. 3 illustrates an embodiment of the hardware architecture of a wearable node 20. The core unit 60 includes a processing unit 40, e.g., microprocessor or microcontroller, a memory unit 62, e.g., RAM or flash memory, and digital-to-analog and analog-to-digital converters 42*a*, 42*b*. The core unit is in charge of sampling, processing and storing sensed data, and of orchestrating ultrasonic networking operations. Specifically, the processing unit executes the system functionalities discussed in Section 2. The communication unit 46 enables ultrasonic wireless connectivity by embedding power and low noise amplifiers 54, 52, and air-coupled ultrasonic transducers 48. A power unit 70 can include a battery 72 to power the wearable node. An optional wireless energy transfer unit 74 can be installed to leverage ultrasonic power transmission to wirelessly charge the node's battery. A sensing and/or actuating unit 80 can incorporate several sensors and actuators according to the specific application design, e.g., accelerometers, ECG, drug pumps and neurostimulators, among others.

Figure 4:
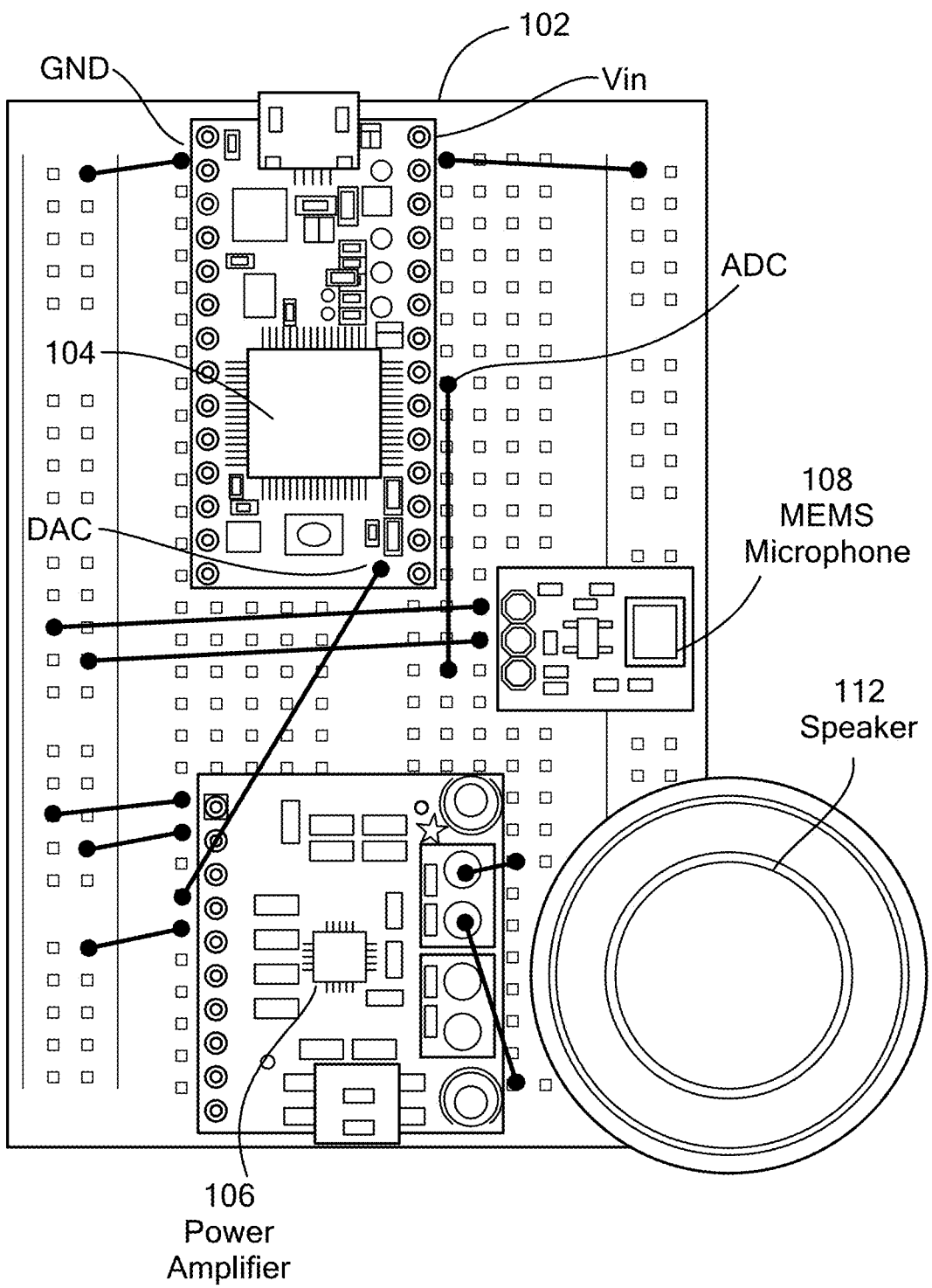
FIG. 4 is an illustration of an ultrasonic communication system prototype.

The architecture in FIG. 3 of the prototype has been implemented based on the Teensy 3.1 platform, a microcontroller development board. The wearable node offers near-ultrasonic capability, by using commercial off-the-shelf (COTS) audio speakers and microphones as air-coupled ultrasonic transducers. FIG. 4 shows the basic circuit design of the wearable node prototype on a solderless breadboard 102. The prototype includes a Teensy 3.1, i.e., the core unit 104, a power amplifier 106, a microphone 108, and small audio speaker 112, i.e., the communication unit. A lithium ion polymer battery, not included in the figure, is connected to the bus strip of the breadboard to power the electronic components. It will be appreciated that these prototype hardware components can be embedded in a customized PCB.

Teensy 3.1. Teensy 3.1 is a small-footprint, i.e., about 3.5×1.8 cm, breadboard-friendly and inexpensive development board, based on a 32 bit ARM Cortex-M4. It comes with 64K of RAM, 256K of Flash, 12 bit DAC, dual ADC, and USB connectivity. Teensy 3.1 can be programmed in C and C++ using Teensyduino, a customized version of the Arduino integrated development environment (IDE), and supports many of the code libraries designed for Arduino and others specifically designed for Teensy, e.g., an audio library, among others. Teensy 3.1 can be powered via USB, or through external batteries connected to the $V_{in}$ and GND pins.

The Teensy 3.1 was selected among other available COTS platforms such as USRP N210, Raspberry Pi, or Arduino Uno. Compared to USRP N210 and Raspberry Pi, where software operations are executed on top of an operating system running on external or internal microprocessor, Teensy 3.1 and Arduino Uno are designed around a low-power microcontroller that provides low-level control of the hardware peripherals. Microcontroller-based platforms offer higher hardware flexibility and computational efficiency that suit the design requirements of wireless wearable devices. Finally, Teensy 3.1 was selected over Arduino Uno because of the more powerful microcontroller and larger available memory that can support high audio sampling rates compatible with the near-ultrasonic communication range, e.g., 44.1 kHz for acoustic frequency up to 22 kHz. Teensy 3.1 still supports the Arduino libraries that can significantly ease the prototyping process of the wearable node.

Power Amplifier. The wearable node includes a small and efficient class D audio amplifier able to deliver a maximum of 1 W into 4 ohm impedance speakers, with a voltage supply of 3.3 V DC, and efficiency up to 80%. The amplifier consumes less than 2 mA of current when quiescent and less than 2 μA in standby mode. In FIG. 4, the right channel of the power amplifier is connected to Teensy via the DAC pin, and to the speakers via the 3.5 mm screw-terminal blocks. The $V_{cc}$ and GND pins are connected to the bus strip to power the device.

Microphone. The input of the wearable node is a tiny breakout board that embeds an ADMP401 MEMs microphone and a low-noise amplifier. The ADMP401 offers a mostly flat bandwidth, i.e., −3 dB roll off, between 100 Hz and 15 kHz, omnidirectional sensitivity pattern, and requires a supply voltage between 1.5 V and 3.3 V DC. Although a microphone with larger bandwidth would perform better, the selected solution is desirable because of the COTS breakout board package that eases prototyping. Moreover, even though with lower sensitivity, the ADMP401 can still detect higher frequency acoustic waves up to 22 kHz. The microphone is connected to one of the analog pins (ADC) available in Teensy 3.1, and is powered by connecting the $V_{cc}$ and GND pins to the bus strip.

Audio Speaker. The output of the wearable remote is a small and compact COTS speaker, Dayton Audio CE28A-4R, with 4 ohm impedance, 4 W maximum output power supported, and flat frequency response between 100 Hz and 15 kHz. The speaker is connected to the power amplifier using 3.5 mm screw-terminal blocks.

It will be appreciated that the hardware architecture can be implemented with other hardware components than those describe in conjunction with the prototype of FIG. 4.

4.1.2 Software Architecture

Figure 5:
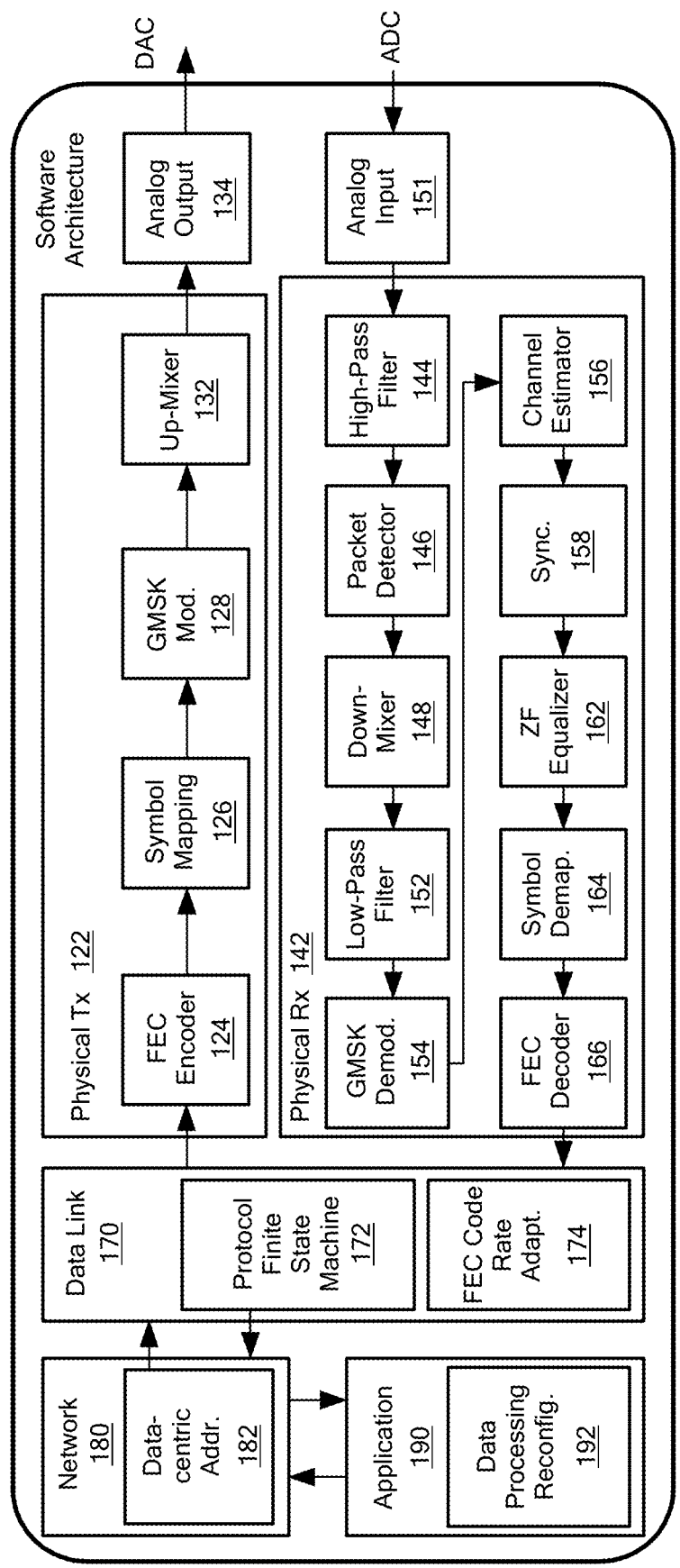
FIG. 5 is a schematic block diagram illustrating a software architecture embodiment of an ultrasonic communication system.

The system framework was implemented in Teensy 3.1 to enable ultrasonic wireless connectivity and networking on the wearable node hardware prototype. FIG. 5 shows a block diagram of an embodiment of a wearable node software architecture that includes (i) narrowband GMSK transceiver with synchronization, channel estimation, equalization, and FEC functionalities at the PHY layer, (ii) polling and ALOHA multiple access protocol with FEC coding rate reactive adaptation at the data link layer, (iii) content-centric addressing at the network layer, and (iv) data processing reconfiguration with fetch and push support at the application layer.

The wearable node functionalities were implemented using Teensyduino, an add-on for the Arduino IDE, leveraging many of the code libraries available for the Arduino platform. Since ultrasonic waves are sound waves at higher frequencies, the PHY layer signal processing was based on the audio library specifically designed for Teensy 3.1. The Teensy audio library includes a set of objects that enable recording, processing, and playback of audio sampled at 44.1 kHz. Objects instantiate specific audio functionalities, e.g., a waveform synthesizer and finite-impulse-response (FIR) filters, while new functionalities can be enabled by creating new objects. A cascade of objects forms a processing chain that performs a set of operations on inputs to produce a desired output. Each object in the chain operates in pipeline on chunks of 128 audio samples, which correspond to 2.9 ms of audio. To guarantee audio continuity, each block must execute its processing operation within 2.9 ms.

In the wearable node implementation, custom-made objects were built that implement specific signal processing operations. Since some computationally expensive operations exceed the audio library time constraints of 2.9 ms, these were implemented outside of the audio library. These are referred to as off-the-chain objects.

Physical Tx. The first object of the PHY layer Tx chain 122 is the FEC Encoder 124. Here, each data packet coming from the data link layer is coded, as discussed in Section 3.1.4, and overhead symbols are appended to the original packet, selecting n=255 symbols and parity symbols t to achieve different coding rates, e.g., 1/2, and 2/3, among others. Because of the computation complexity of RS coding, the FEC Encoder is implemented as an off-the-chain object. The coded packet is then passed to the Symbol Mapping object 126 that inputs the audio stream in the processing chain. Here, the coded packet is serialized, i.e., converted into a stream of bits, differentially encoded, and transformed into a non-return-to-zero (NRZ) signal. The NRZ signal is then GMSK modulated by the GMSK Modulator object 128 and up-converted to the carrier frequency by the Up-Mixer object 132. The modulated and up-converted waveforms are passed to the Audio Output object 134, i.e., a system API that interfaces the system with the embedded DAC (42a, FIG. 3), digital-to-analog converted and transmitted through the power amplifier (54, FIG. 3) and audio speaker (48, FIG. 3).

Physical Rx. The received acoustic signal is converted into an electrical signal by the MEMS microphone. The signal is amplified by the LNA (52, FIG. 3), and analog-to-digital converted by the Teensy 3.1 ADC at 44.1 kHz. The Audio Input object 151 is a system API that interfaces the system with the embedded Teensy 3.1 ADC (see also 42b, FIG. 3), and inputs the audio stream into the PHY layer Rx chain 142. The received digital signal is first high-pass filtered by the High-pass Filter object 144 to eliminate low-frequency noise and interference, i.e., external human voice and ambient noise. The Packet Detector 146 processes the input signal to detect incoming packets using an energy-based approach to check whether there is energy at the expected carrier frequency. The incoming packet is then down-converted by the Down Mixer 148, i.e., converted into a complex in-phase/quadrature baseband signal, and low-pass filtered at filter 152 to eliminate undesired higher-frequency harmonics introduced by the nonlinearity of the down-conversion operation.

Channel estimation, synchronization and equalization operations normally follow down-conversion and are applied to the complex baseband signal. However, these operations are computationally expensive, and their execution exceeds the audio library time constraints of 2.9 ms. To overcome this limitation, the complex baseband signal is first demodulated in the GMSK Demodulator object 154 to extract the phase variation that carries the coded information bits. Then, the computationally expensive operations are executed off-the-chain. The Channel Estimator object 156 estimates the CIR using the packet preamble as training sequence, as discussed in Section 3.1.3, while the Synchronizer object 158 attempts to achieve fine synchronization through the PN-based mode discussed in Section 3.1.2. The ZF Equalizer object 162 filters the input for ISI recovery, as discussed in Section 3.1.3. The equalized symbols are demapped at demapper 164 into a bitstream, collected into a packet structure, and passed to the FEC Decoder object 166. Here, FEC decoding operations attempt to correct potential bit errors, as discussed in Section 3.1.4. Finally, the error-corrected packet is passed to the data link layer 170.

Data Link Layer. One embodiment of the wearable node data link layer 170 is implemented in a Finite State Machine (FSM) block 172 that can include two of the MAC protocols discussed in Section 3.2, polling and ALOHA. Polling can be exclusively used in M/S configuration, while ALOHA works in both M/S and P2P configurations. The wearable remote data link layer also implements a PHY layer adaptation 174 to optimally select the FEC coding rate that minimizes the number of retransmissions. The MAC protocol FSM 172 is also in charge of coordinating the PHY layer receiving and transmitting operations. During packet transmission, the MAC FSM collects data from upper layer protocols and creates the data-link-layer packet. The packet starts after a preamble that enables coarse and fine synchronizations and allows the receiver to detect an incoming packet and identify the exact packet start time. The packet payload is followed by a 16-bit checksum that is used at the receiver to identify if the packet has been correctly received. The packet is then forwarded to the PHY layer Tx chain 122, where it is encoded in a digital waveform before being transmitted. At the receiver side, the MAC FSM detects the received packet based on information coming from the Packet Detector block 146 and triggers the PHY layer 142 to start processing the received waveform. The MAC FSM is also in charge of checking the packet checksum, and forwarding the received data to the upper layer.

Network Layer. One embodiment of a wearable node network layer 180 can implement the content-centric addressing scheme 182 discussed in Section 2.3. Each content object can be mapped into a binary mask, where it is represented by the bit position in the mask, e.g., '0001' for the "heart rate" content, '0010' for the "footsteps" content and '0100'. The binary mask has variable length and can be adjusted to match the number of entities available in the network.

In an M/S configuration, a node joining the network is first paired with the master node. The master maps the content available in the new node into the binary mask, and broadcasts the updated mapping to all the nodes in the network. Each node builds a local mask based on the entities that it possesses. To request an entity, the master broadcasts a request message containing a request mask with '1' set in the position mapped to the desired content. For example, to retrieve heart rate and footsteps content, the '0011' request mask is broadcasted in the network. Slave nodes compare the request mask to their local masks, and forward the matching contents, if any. In a P2P configuration, the pairing operation is replaced by a discovery operation, and the binary mask is maintained distributively in the network. When a new node joins the network, it requests the current mask mapping from neighbor peer nodes, updates it with the contents it holds, and then broadcasts the updated mapping.

Application Layer. In one embodiment, a wearable node application layer 190 can implement real-time modular reconfiguration functionalities 192, as discussed in Section 2.4, and can support both fetch and push data collection operations. Following is a list of some examples of the primitive blocks implemented in this prototype:

fir_filter: a FIR filter that accepts parameters defining filter specifications, i.e., cutoff frequencies.

find_peaks: finds peaks in a 1-dimensional data sequence given a threshold value.

find_next_extr: returns the next local extremum, i.e., maximum or minimum, after or before a peak.

calculate_distance: calculates distances between time instants, e.g., peak-to-peak.

average and std, return the average and standard deviation of the input data.

count_events: implements a counter of events, e.g., how many times a value exceed a given threshold.

Based on this modular approach, applications can be represented by chains of binary sequences, i.e., keys. Each primitive function is mapped to a binary key. A concatenation of keys represents a concatenation of operations, and therefore represents an application. The application is encapsulated into reconfiguration packets and transmitted over-the-air. The receiving node extracts the binary keys, and feeds these into an FSM where each state represents a primitive block function. By parsing the consecutive function keys, the FSM transitions from state to state, processing inputs and producing outputs. Inputs and outputs of each function are mapped to binary keys as well, and are implemented in a C-struct output struc that contains a pointer to an array, and a binary key variable. The input and output keys allow parametrically passing data between functions. Absolute inputs, those coming from the sensing hardware, are also represented by binary keys, and can usually be fed to the first block of the application chain. Finally, function parameters can be serialized and also passed in the form of binary strings.

As a proof-of-concept, some applications were developed based on the primitives discussed above.

Figure 6:
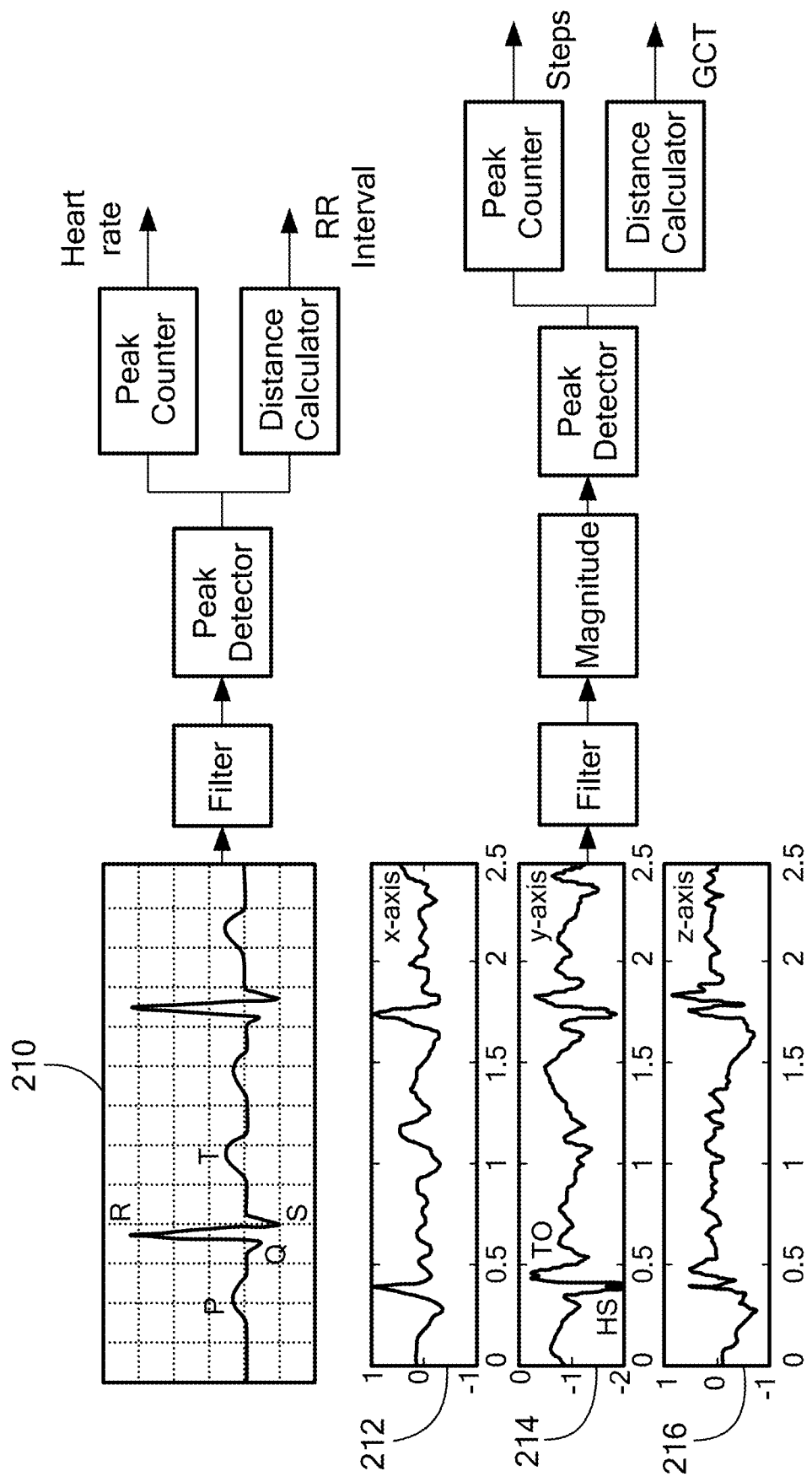
FIG. 6 is a schematic illustration of primitive blocks of a heart rate and RR interval monitor (top) and footstep and GDT monitor (bottom) using an ultrasonic communication system.

Electrocardiogram (ECG) Processing. Consider a single-electrode ECG signal. FIG. 6 shows a template signal 210 with five labelled characteristic waveforms, i.e., P, Q, R, S and T, that correspond to three electrical events during one heartbeat, i.e., atrial contraction (P), ventricular contraction (QRS) and ventricular recovery (T). The first application measures the heart rate in beat-per-minute [bpm]. This is done following two different approaches. The first approach, here R method, counts the number of peaks, R waves, in a 6-second trace and multiplies the result by 10. The second approach, here RR method, finds the number of heartbeats per second by inverting the average of the RR interval duration, i.e., distance between two consecutive R waveforms in the trace, and multiplies this by 60. This approach has higher complexity with respect to the R-method, but results in higher resolution, i.e., 1 bpm against 10 bpm of the R method. The second application measures average and standard deviations of temporal separation between electrical events in the ECG. For example, the distance between peaks, i.e., R waves gives the RR interval duration. The mean and standard deviation of the RR interval give important information about potential heart arrhythmias or other malfunctioning. FIG. 6 (top) shows the simplified primitive block sequences of the R method heart rate detector and the RR interval monitor applications.

Accelerometer Processing. The accelerometer trace in FIG. 6 shows the frontal acceleration on the x-axis 212, the vertical acceleration on the y-axis 214, and the lateral acceleration on the z-axis 216. Two main events are labeled in the y-axis that occur during a single step, i.e., heel strikes (HSs) and toe-off (TO), that correspond to the instants at which the foot touches the ground, and the instants at which the foot leaves the ground, respectively. Based on this, the first application calculates the magnitude of the acceleration from the three-axis components, low-pass filters it to remove high frequency noise, and counts the number of peaks in the resulting signal, i.e., the number of HSs. The peaks within a time interval represent the number of footsteps performed by the patient. The second application measures average distances between events in the accelerometer trace. For example, the distance between non-consecutive peaks in the acceleration magnitude gives the gait cycle time (GCT), i.e., time between consecutive HSs on the same foot. GCT offers a measure of the motor degradation of patients affected by Parkinson disease. FIG. 6 (bottom) shows the simplified primitive block sequences of the footstep counter and the GCT monitor applications.

4.2 Wearable Master Prototype

Figure 7:
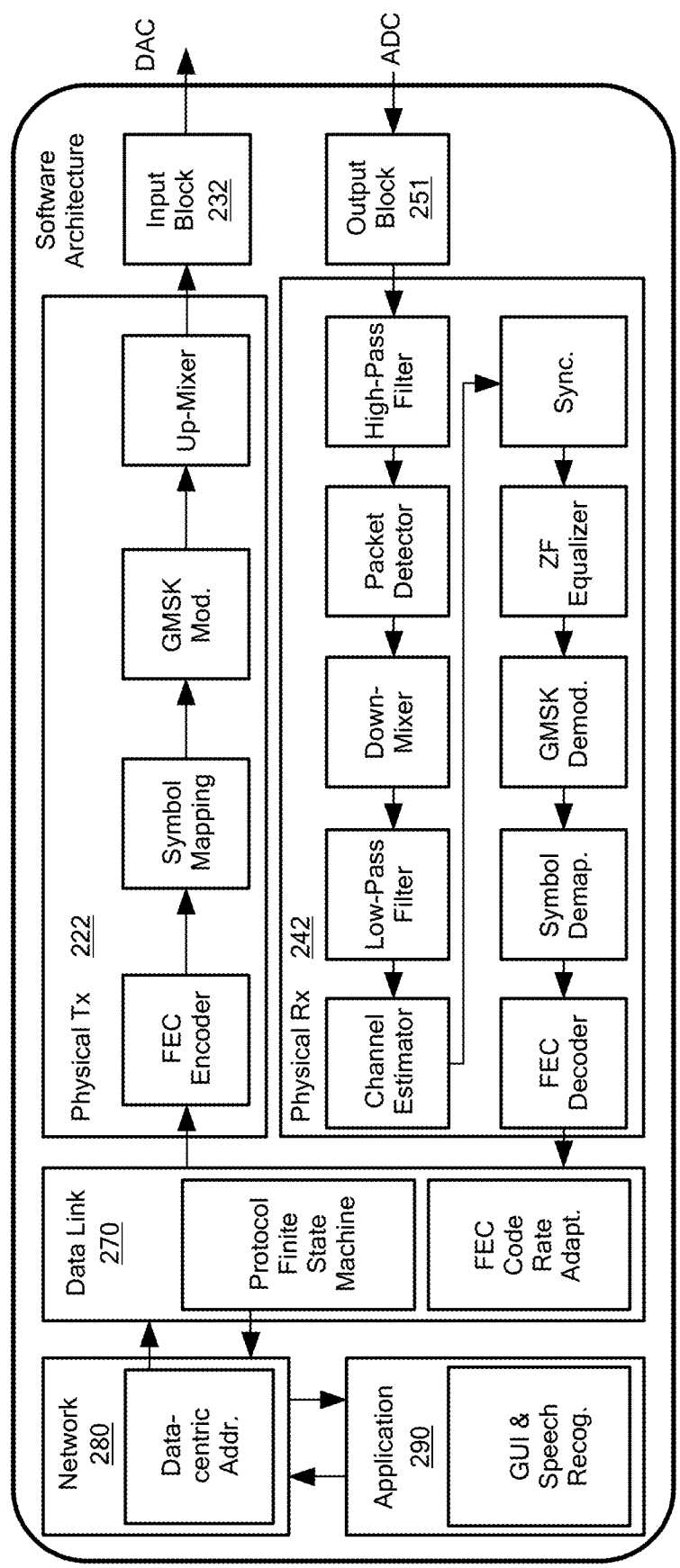
FIG. 7 is a schematic block diagram illustrating a software architecture embodiment of an ultrasonic communication system.

An embodiment of a wearable master node prototype was implemented on the iOS 8 platform for Apple iPhone smartphones. The prototype comprises an app running on an iPhone smartphone that implements the system multi-layer functionalities. FIG. 7 shows an embodiment of the software architecture of the wearable master prototype that includes (i) narrowband GMSK transceiver with synchronization, channel estimation, equalization, and FEC functionalities at the PHY layer, (ii) polling and ALOHA multiple access protocol with FEC coding rate reactive adaptation at the data link layer, (iii) content-centric networking at the network layer, and (iv) a graphic user interface (GUI) and speech recognition functionalities at the application layer that allow users to interact with the wearable network.

The iOS prototype can communicate wirelessly with the wearable nodes through an ultrasonic narrowband GMSK link, using the phone's embedded microphone and speaker. The software prototype was developed in Objective-C programming language using Xcode 6 integrated development environment (IDE), and leveraging the Xcode storyboard feature for developing the graphic user interface (GUI). Also used were (i) the vDSP library of the iOS Accelerate framework that implements digital signal processing (DSP) operations, (ii) Novocaine, a high performance audio library that enables record/play audio functionalities, and (iii) wit.ai framework that offers speech recognition services.

vDSP Library. The vDSP library is part of the Accelerate framework available in iOS, and provides several DSP functionalities including vector and matrix arithmetic, Fourier transforms, convolution and correlation operations between real or complex data types. The vDSP functionalities can be leveraged to perform arithmetic operations and correlations on real and complex vectors in the PHY layer.

Novocaine. Novocaine is a high performance audio processing library for iOS. Novocaine hides all the low-level audio implementation details, giving simple block-based callbacks that are called when audio comes in, and when audio needs to go out. Specifically, a Novocaine object, i.e., the Audio Manager, offers InputBlock and OutputBlock callbacks, inside which the DSP code can simply be placed for processing input and output data.

Wit.ai Framework. Wit.ai provides natural language processing in the form of multi-platform APIs, which are used to integrate voice command in the system. Wit.ai allows developers to create commands, and to match these commands with intents. A command is what the user would say to trigger an operation, while the intent represents the operation itself. Voice commands are sent to the wit.ai server, and the intent with maximum confidence is returned as a response. Since wit.ai requires Internet connectivity to submit a request and receive a response, voice commands are available only through the wearable master with Internet connectivity. However, a lightweight embeddable version of wit.ai can be provided to make it possible to address voice commands directly to the wearable nodes.

PHY Layer Tx/Rx. The PHY layer Tx 222 and Rx 242 are implemented in two classes named PHYLayerTx and PHYLayerRx, respectively. Here, the Novocaine Audio Manager triggers the InputBlock 232 and OutputBlock 251 callbacks to record and play audio, and the vDSP functions process the input and output data. At the transmitter, the PHYLayerTx class gets the data from the data link layer 270, generates the GMSK waveform, and then passes it to the Audio Manager. The latter transmits the GMSK waveform through the speaker. At the receiver, the operations in PHYLayerRx match those implemented in the wearable node PHY layer 242, discussed in Section 3.1.2 (see also FIG. 3). Because of the less stringent memory and processing constraints of the iOS platform, here the packet can be entirely stored in memory after being detected, and decoded right after. Moreover, channel estimation, synchronization and equalization operations follow the down-conversion, and are applied to the complex baseband signal.

Data Link and Network Layer. The wearable master data link layer 270 can implement polling and ALOHA MAC protocols, as well as FEC coding rate adaptation. The MAC functionalities can be implemented in a class named MACLayer, where a FSM implements the MAC protocol operations. The wearable master network layer 280 can implement the same content-centric addressing scheme as in the wearable node prototype, with the exception that here the centralized mapping functionalities are also implemented.

Figure 8:
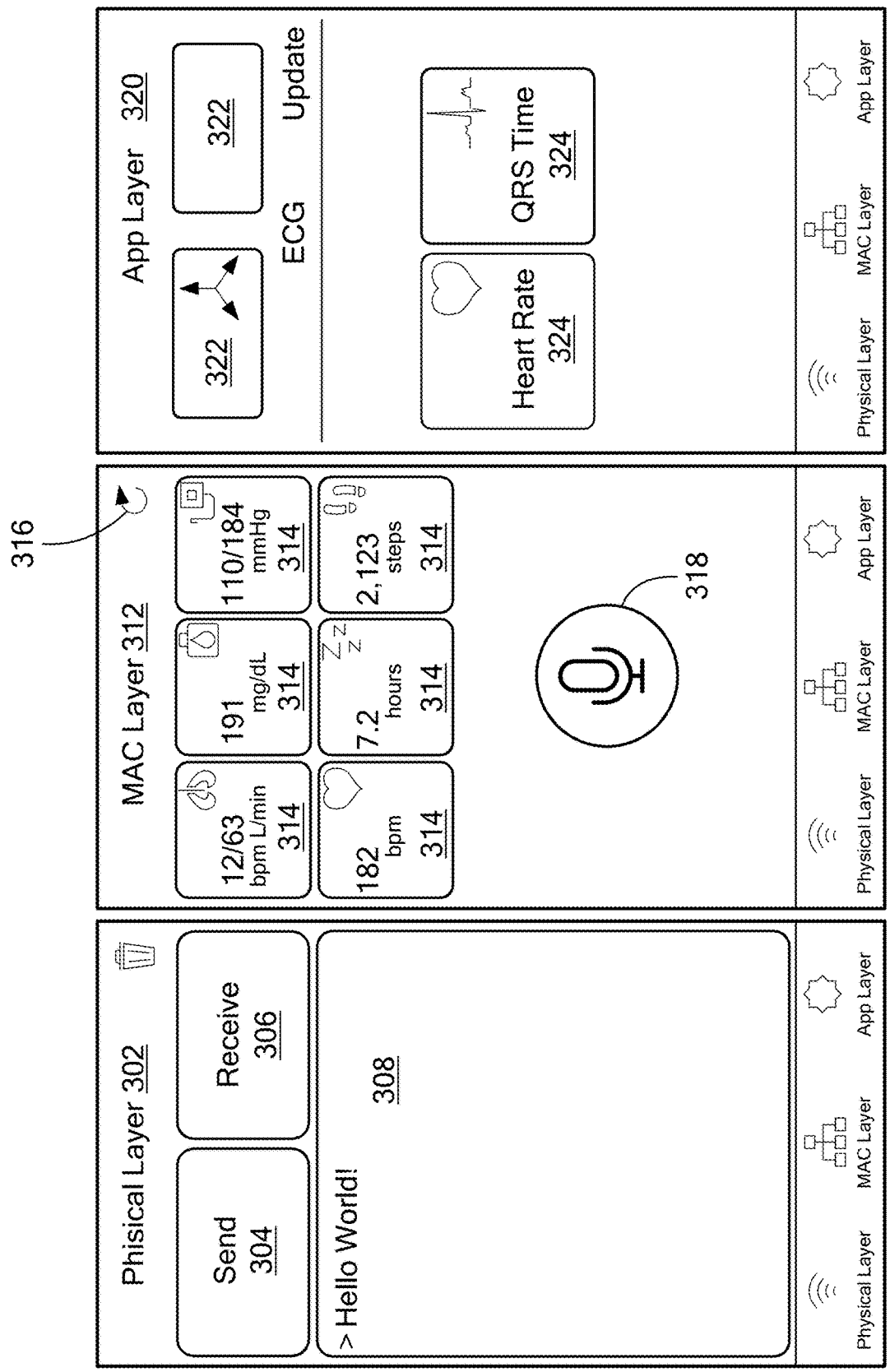
FIG. 8 is a schematic illustration of an embodiment of a graphical user interface for a physical layer (left), a MAC layer (center), and an application layer (right)

Application Layer. The wearable master application layer 290 can comprise a graphical user interface (GUI) and a set of witai commands that allow interaction with the system multi-layer functionalities. In one embodiment, the GUI's principal element is a three-tab TabViewController class. The first tab 302, shown in FIG. 8 (left), contains a PHYViewController object. It inherits from UIViewController, i.e., a basic view controller in iOS, and is implemented for testing the PHY layer performance. PHYViewController accommodates two UIButtons 304, 306 that allow transmitting and receiving random data, and a console-like UITextView 308 that displays the transmitted packets, and the BER information of the received ones. The second tab 312 contains a MACViewController object that inherits from UIViewController and allows the user to test the MAC Layer functionalities by requesting, receiving and visualizing sensed data coming from the deployed wearable nodes. The MACViewController embeds a UICollectionView, a collection of objects 314 that represent the sensed data. In FIG. 8 (center) six objects 314 in the collection are shown, which are associated with the number of footsteps, the number of sleep hours, the heart rate, the breath rate and the respiratory minute volume, the glucose level in the blood and the diastolic/systolic blood pressure. A UIBarButtonItem refresh object 316 allows fetching all the monitored data. A WITMicButton 318, defined in the wit.ai framework, enables voice command processing. The current implementation supports several vocal commands that allow to fetch any of the monitored medical data, e.g., "measure my blood pressure", or "for how long did I sleep last night?", among others. The third tab 320 contains an APPViewController object that gives access to application layer reconfiguration functionalities discussed in Section 2.4. In the APPViewController, the applications are grouped based on the sensing unit that provides the required input data, e.g., accelerometer and ECG. Each UIButton 322 represents a group of applications, and it gives access to a PopViewController object that shows the available applications 324 in that group. Users can select which application to run on the wearable node. For example, FIG. 8 (right) shows how a user can select to install heart rate or RR interval monitor on wearable remotes equipped with ECG.

5. Performance Evaluation

The feasibility of ultrasonic communications for wearable devices is demonstrated through testbed experiments, and the performance of the prototypes discussed in Section 3 are evaluated. First, the physical layer performance of the prototypes is evaluated in terms of BER as a function of (i) the signal-to-noise ratio (SNR) at the receiver, and of (ii) FEC coding rate. Then, it is shown how the system MAC protocols allow network nodes to coexist while enabling users to efficiently access the sensed medical parameters. Finally, the reconfigurable data processing of the system is leveraged to install and run three applications built using the set of primitive blocks. The three applications are evaluated in terms of processing accuracy, i.e., the displacement between the obtained outputs and the expected ones.

5.1 PHY Layer Performance

Figure 9:
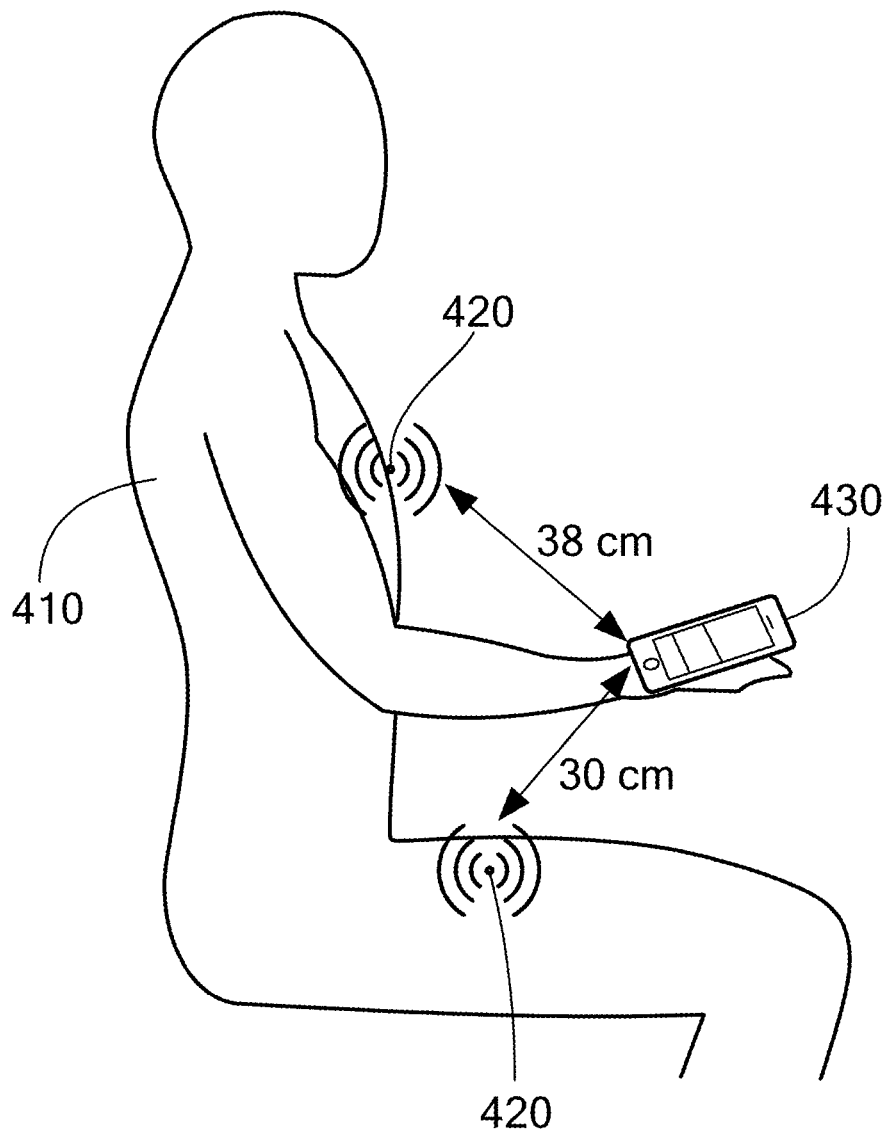
FIG. 9 is a schematic illustration of a near-line-of-sight (nLOS) experimental setup.
Figure 10:
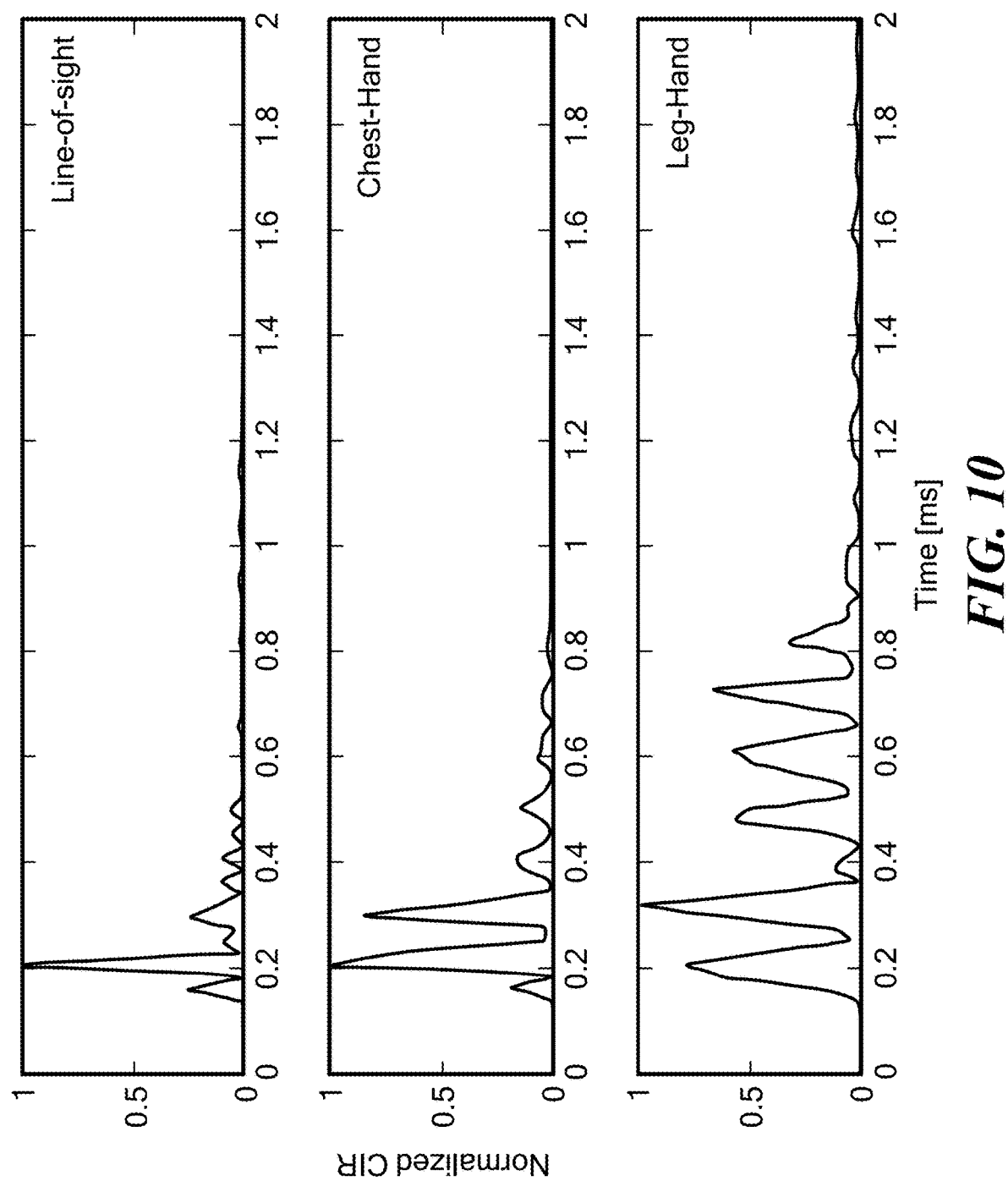
FIG. 10 is a graph of ultrasonic in-air CIR for line-of-sight (LOS) (top), chest-hand nLOS (center), and leg-hand nLOS (bottom)

Experiment Setup. The experiment setup consists of a wearable node communicating bidirectionally with a wearable master in two different scenarios, line-of-sight (LOS) and near-line-of-sight (nLOS). In the LOS scenario the two devices are aligned, 50 cm apart, without obstacles in between, so as to minimize reflections and scattering. In the nLOS scenario, the wearable nodes 420 are located along the body 410 of a user, on the chest and on the right leg, as shown in FIG. 9. The wearable master node 430, located at the smartphone, is held in the user's right hand. Under this setup, objects within the propagation area cause reflections and scattering that introduce ISI and degrade the communication performance. FIG. 10 shows the uplink CIRs of the three scenarios discussed above. It can be observed that, in the LOS scenario, the CIR contains a single dominant component. In the nLOS scenario, because of the multipath, there are multiple components that contribute to ISI distortion at the receiver. In particular, in the chest-hand setup, the CIR clearly presents a second path, most likely because of a reflection from the user's hand, while in the leg-hand setup up to 6 paths can be counted, most likely caused by multiple reflections from the user's trunk and hand. The coherence bandwidth in these three scenarios is approximately 21 kHz, 14 kHz, and 6 kHz, respectively.

For each BER measurement up to 600 packets of 32 bytes, i.e., approximately 256 kilobits, are transmitted containing pseudorandom-generated raw data. The experiment was performed in an indoor room where the temperature was about 21° C. and the relative humidity was around 30%. The physical layer was configured such that each GMSK symbol is represented by 16 samples. The sample rate is set to 44.1 kHz as required by the audio hardware in use. Based on this, the raw physical layer data rate, obtained as the ratio between sample rate and sample per symbol, is approximately 2.76 kbit/s. The GMSK BT product is fixed to 0.7, which represents a good tradeoff between ISI distortion and spectral efficiency. The resulting signal bandwidth is of about 2 kHz, which is lower than the coherence bandwidth of the three experimental setups, thus complying with the definition of a narrowband transmission scheme. The central frequency is set to 18 kHz, which, while still in the audible frequency range, represents a good tradeoff between low audibility, fair propagation efficiency, and fair acoustic generation and detection with the COTS microphone and speaker in use. Specifically, it was found that 18 kHz is the highest frequency, given the spectral response of microphones and speakers in use, for which highly reliable communications could be obtained, i.e., relatively low BER, in the range of distances of interest, i.e., up to 1 m. At the same time, the signal transmission is almost inaudible by the user wearing the device. A 64-bit PN-sequence is used as preamble for synchronization and channel estimation purposes.

Figure 11:
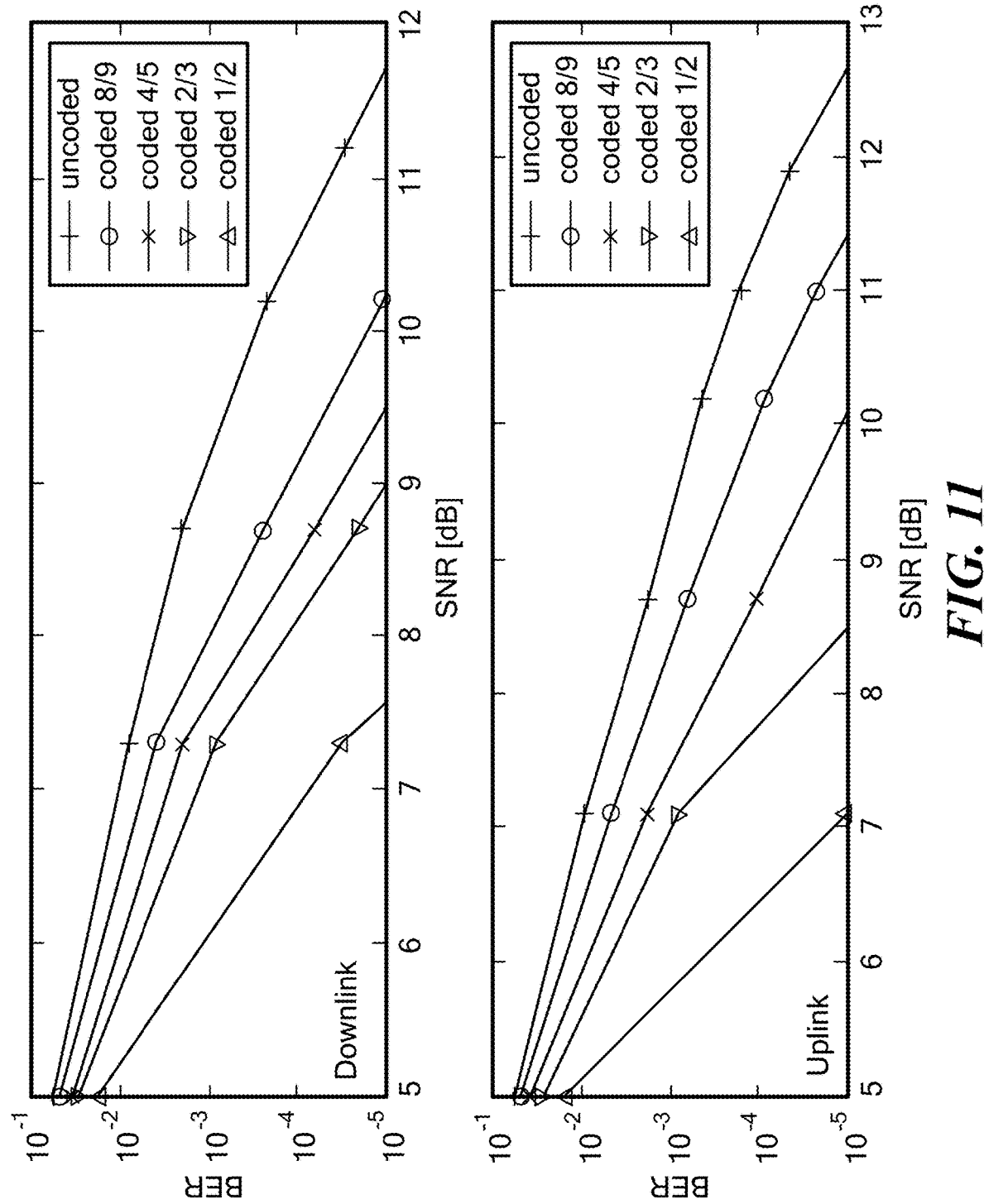
FIG. 11 is a graph of bit error rate (BER) of a downlink (top) and uplink (bottom) in LOS as a function of the signal-to-noise ratio (SNR) for different coding rates.

BER Performance in LOS. FIG. 11 (top) shows the BER results for the downlink, i.e., from the wearable master to the wearable node, and the performance of an uncoded transmission scheme is compared to four coded transmission schemes with coding rates in {8/9, 4/5, 2/3, 1/2}. The information rate for the five transmission schemes ranges from 2.76 kbit/s for the uncoded transmissions to 2.45 kbit/s for coding rate 8/9, 2.20 kbit/s for coding rate 4/5, 1.84 kbit/s for coding rate 2/4, and 1.38 kbit/s for coding rate 1/2. FIG. 11 (bottom) shows the same comparison for the uplink, i.e., from the wearable node to the wearable master. The SNR is calculated at the receiver as the ratio between the received average signal power and the average noise power measured after amplification and high-pass filtering. The measured SNR is varied by reducing the signal power driving the transmitter speaker. In the downlink, this is done by reducing the volume of the smartphone speaker, while in the uplink, the signal full-scale is reduced at the input of the amplifier. The maximum power is selected such that the transmitted sound results are inaudible to people in proximity of the transmitter.

From FIG. 11, it can be observed that, as expected, the BER is a decreasing function of the SNR, and that the FEC scheme mitigates the channel distortion by recovering part of the channel errors. At 5 dB SNR the BER is too high for the FEC to have an impact on the communication performance. Over 5 dB SNR, higher coding rate transmissions have clearly better mitigation performances, thus lower BER.

By measuring the power at the output of the wearable node amplifier, it can be shown how the prototypes achieve 2.76 kbit/s on an uncoded uplink transmission, with a $10^{-5}$ BER, using a transmission power of 20 mW, i.e., 13 dB SNR at the receiver. The transmission power can be lowered by compensating with lower FEC coding rate, thus reducing the information rate. For example, in the current implementation, for a transmission power of 10 mW, i.e., 7 dB SNR, the prototypes achieve 1.38 kbit/s with a $10^{-5}$ BER using a coding rate of 1/2.

By using for the first time a GMSK scheme for the near-ultrasonic frequency range, the prototypes achieve relatively a high-data rate, and ensure virtually inaudible click-free transmission because of the GMSK phase-continuity as discussed in Section 2.1.1.

Figure 12:
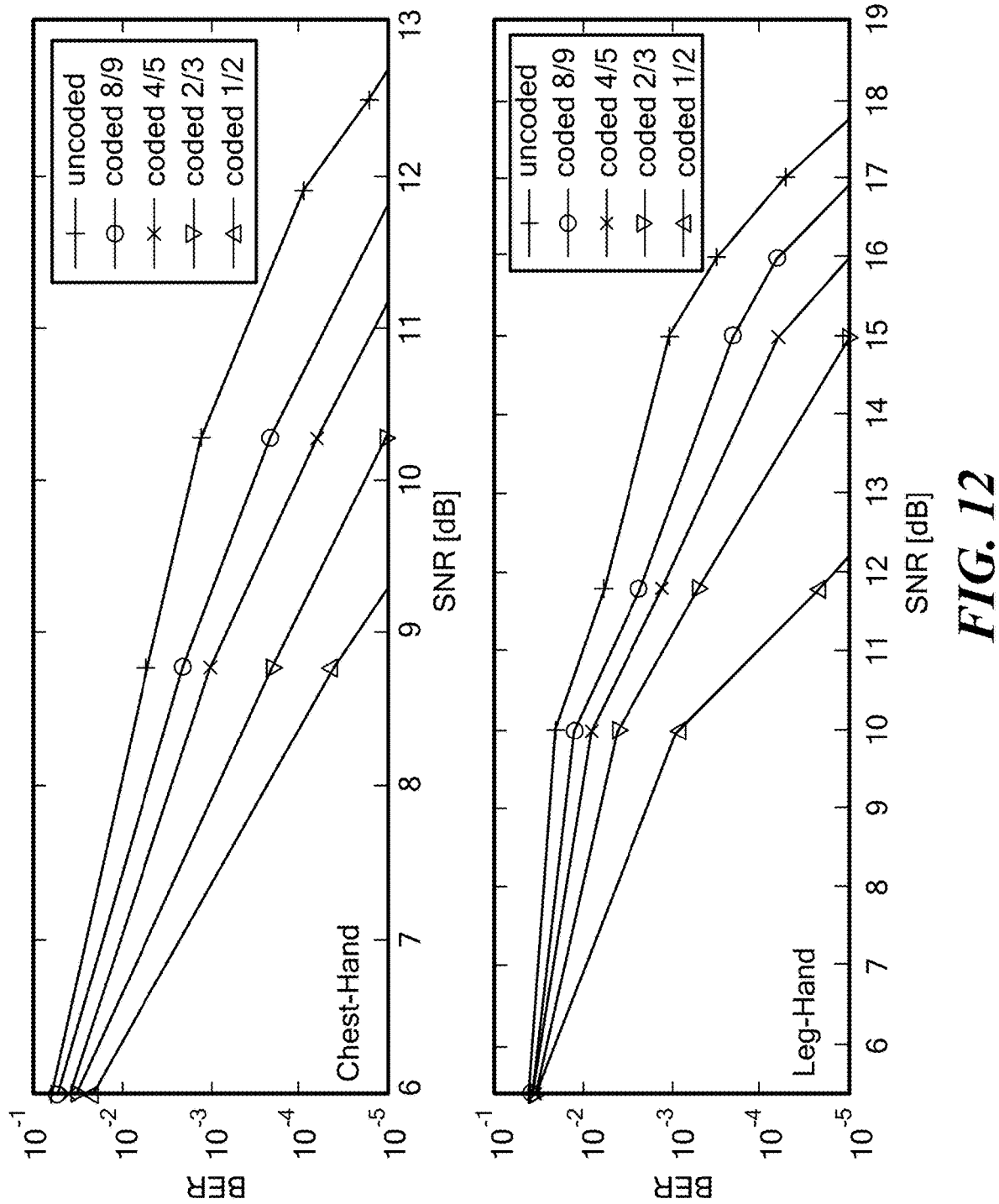
FIG. 12 is a graph of BER of the chest-hand (top) and of the leg-hand uplinks as a function of the SNR for different coding rates.

BER Performance in nLOS. FIG. 12 shows the BER performance of uplink transmissions in nLOS scenario chest-hand setup (top) and leg-hand setup (bottom). It can be observed that, while the curves follow the same pattern as in the LOS scenario, the corresponding BER levels are higher because of the worse channel conditions. The BER in the chest-hand scenario is slightly higher than the LOS one, i.e., about 1 dB more of SNR is required for the same BER. Differently, in the leg-hand scenario an increase of 4 dB SNR is needed to achieve the same BER performance of the LOS scenario. In the chest-hand uplink, the prototypes achieve 2.76 kbit/s with a $10^{-5}$ BER using a transmission power of 45 mW, i.e., about 13 dB SNR at the receiver, while the same BER is obtained with 45 mW transmission power, i.e., approximately 9 dB SNR at the receiver, halving the data rate through FEC coding. In the leg-hand uplink, $10^{-5}$ BER is obtained with a transmission power of 250 mW, i.e., about 18 dB SNR at the receiver, for uncoded transmission at 2.76 kbit/s, and 130 mW of transmission power, i.e., approximately 12 dB SNR at the receiver, for coded transmission at 1.78 kbit/s.

These results show how multipath effect and higher attenuation caused by the user's clothing require higher power transmission as compared to the LOS scenario. Even though ultrasonic signals are further attenuated by solid materials, they can still be used to communicate over short distances through clothing. In general, the transmission power can be reduced by using speakers and microphones with wider flat bandwidth or custom-made optimized ultrasonic transducers. In fact, a significant portion of the transmission power is lost during the electro-acoustic conversion in the COTS speaker and microphone used in the prototypes, which are not designed to operate efficiently at near-ultrasonic frequencies.

5.2 MAC Layer Performance

The performance of the MAC layer protocols implemented on the prototypes, i.e., polling and ALOHA, was evaluated in terms of data delivery delay, and packet drop rate as a function of the number of nodes in the network.

Experiment Setup. A M/S configuration was set up where devices lay in nLOS on a 2-dimensional surface, and each wearable node was positioned 40 cm apart from the wearable master. The experiment collected data at the wearable master from up to four wearable nodes using polling or ALHOA MAC protocols. Six different parameters were considered than can be fetched, and these were distributed among four wearable nodes, i.e., numbers of footsteps and the number of sleep hours in Node 1, heart rate and the diastolic/systolic blood pressure in Node 2, breath rate/ respiratory minute volume in Node 3, and glucose level in the blood in Node 4. Each packet contained 10 bytes of information, i.e., before FEC coding.

Figure 13:
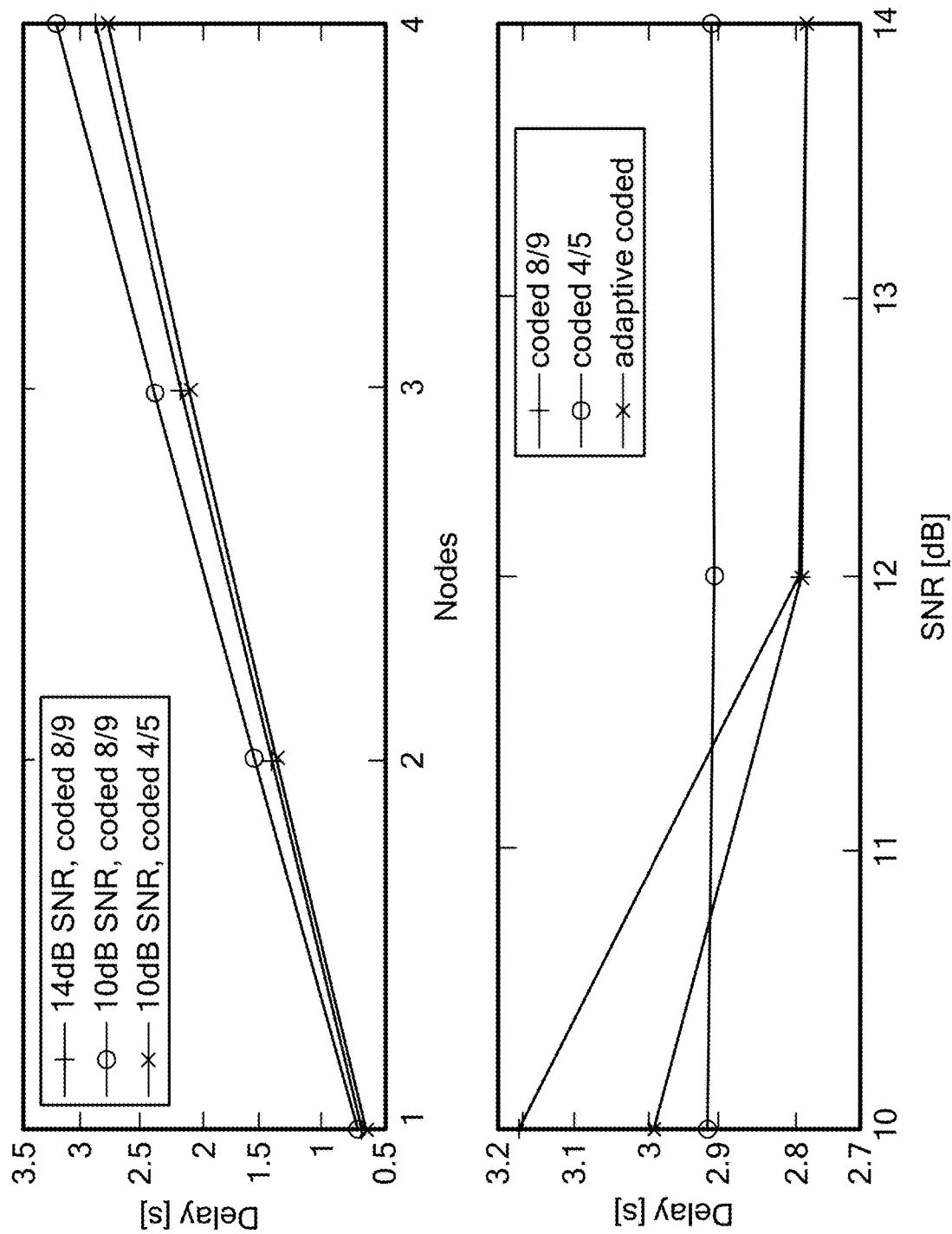
FIG. 13 is a graph of polling data delivery delay as a function of number of nodes for different level of SNR and coding rates (top), and as a function of the SNR for non-adaptive and adaptive scenarios.

Adaptive Polling. Using polling protocol, the wearable master fetched data from one node a time, and wearable nodes were addressed through physical addresses, e.g., node ID. The PHY layer adaptation allowed reactively adapting the FEC coding rate based on the packet drop rate experienced at the wearable master to minimize the number of consecutive retransmissions. Specifically, every time the wearable master retransmitted a fetching packet a lower coding rate was used in {8/9, 4/5, 2/3, 1/2}. The maximum number of retransmissions for each fetch command was fixed to four. The protocol was evaluated in terms of data delivery delay, which was defined as the time between the instant when the first fetching packet is transmitted by the wearable master and the instant when the last data packet is correctly received at the wearable master. FIG. 13 (top) shows the polling data delivery delay as a function of the number of nodes in the network for two levels of SNR measured at the wearable master, i.e., 10 dB and 14 dB, and two coding rates, i.e., 8/9 and 4/5. As expected, since each node in average was granted the same time to transmit, it can be observed that the delivery delay increased linearly with the number of nodes in the network. Moreover, since retransmissions were only caused by the channel conditions, i.e., there were no collisions among different users, the delivery delay decreased by increasing the SNR or the coding rate. FIG. 13 (bottom) shows the delivery delay as a function of the SNR for two fixed coding rates, i.e., 8/9 and 4/5, and for the adaptive scenario. It can be observed that at lower SNR, a coding rate of 8/9 gave delivery delays higher than coding rate 4/5 because of the frequent retransmissions due to higher BER at the PHY layer. On the contrary, for higher SNR, a coding rate of 4/5 introduced more overhead than needed, giving higher delivery delays than a coding rate of 8/9. As expected, the adaptive scenario resulted in delivery delays in between the two fixed coding rate scenarios.

Figure 14:
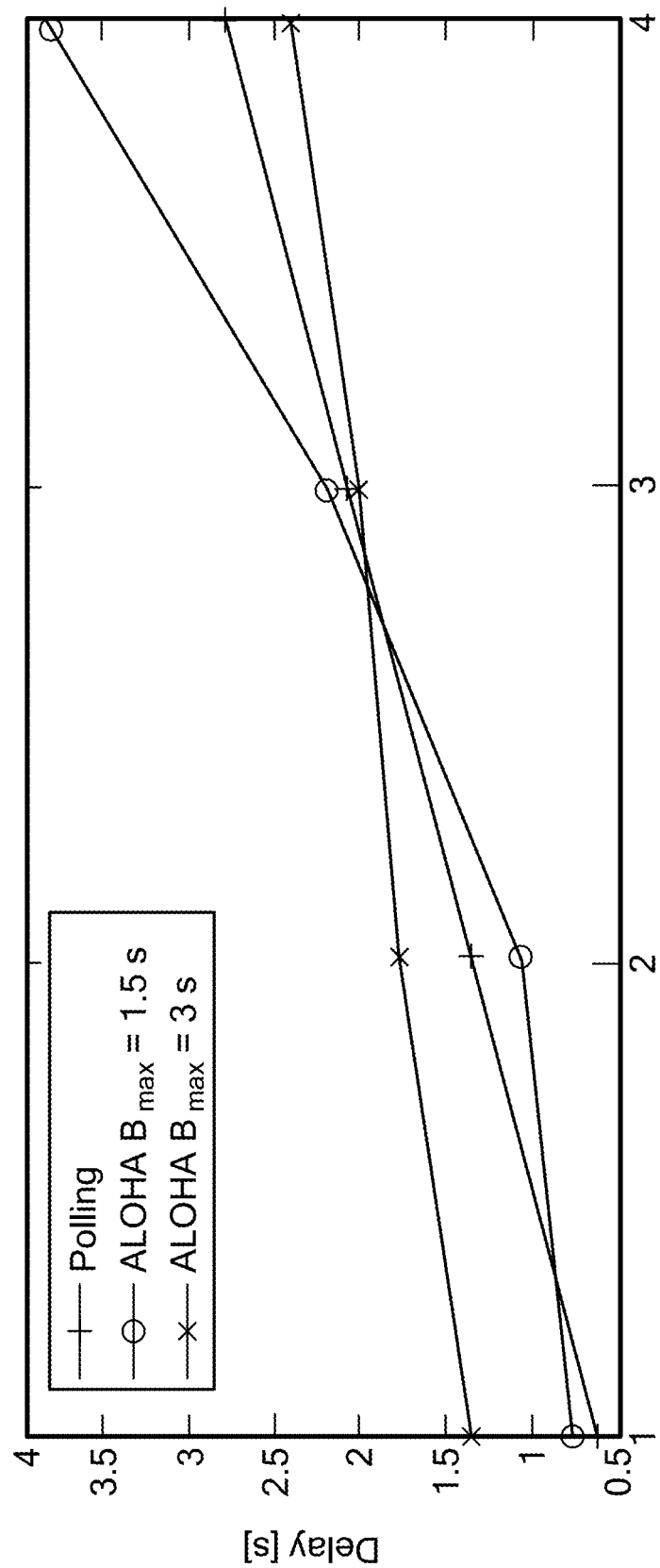
FIG. 14 is a graph of ALOHA data delivery delay as a function of number of nodes for different $B_{max}$, compared to polling.

ALOHA. With ALOHA, the content-centric addressing scheme discussed in Section 3.1.2 was used. Hence, the wearable master broadcast a request message to fetch data from multiple wearable nodes. The wearable nodes transmitted the requested data, if available, by accessing the channel randomly. Finally, the backoff time between transmissions was selected from 0 to a maximum backoff $B_{max}$, and was varied during the experiments, while fixing the SNR to 14 dB and FEC coding rate to 8/9. FIG. 14 shows the data delivery delay as a function of the number of nodes in the network for two different values of $B_{max}$, i.e., 1.5 s and 3 s. The results were compared with the data delivery delay experienced by the polling protocol for 14 dB SNR and 8/9 coding rate. When the number of nodes in the network was lower than three, it can be observed that $B_{max}$=1.5 s gave a lower delay than $B_{max}$=3 s. Here, a higher $B_{max}$ increased the probability of selecting a higher backoff time, leading to channel underutilization. On the other hand, for a number of nodes equal to three or higher, $B_{max}$=1.5 s gave a high probability of collisions, thus a higher delay due to retransmissions.

5.3 Data Processing Performance

To test the effectiveness of the application layer reconfiguration functionalities, the data processing accuracy was evaluated in terms of displacement between the obtained outputs, i.e., what the application reads on a given sensor trace, and the expected ones, i.e., what the application should read on that given sensor trace. Three applications were considered, two running on ECG-equipped sensor nodes, i.e., heart rate monitor, ECG RR interval monitor, and one running on accelerometer-equipped sensor nodes, i.e., footstep counter.

ECG Processing. To show a fair comparison, the application layer data processing was fed with reference raw sensor data that were externally recorded and then loaded in the wearable node memory. For the ECG-based applications, traces from the MIT-BIH Normal Sinus Rhythm Database were used, which collects ECG recording from patients that were found to have no significant arrhythmias. The MIT-BIH database also specifies heart rate and RR interval of the traces that can be used as a reference. The traces were sampled at 128 Hz. Ten one-minute long traces from the MIT-BIH database were extracted and loaded on the wearable node. Table 1 shows the heart rate estimation of the wearable node using the R method, second column, and RR method, third column, discussed in Section 3.1.2. These were compared with the heart rate reference provided by the MIT-BIH database, fourth column. The first column shows the database trace ID. It can be observed that both R method and RR method give a good estimate of the reference heart rate, offering an average accuracy of 96.1% and 98.7%, respectively.

Table 2 shows the RR interval mean µ and standard deviation σ estimated by the wearable node, second and fourth columns, and compares these with the RR interval reference statistics provided by the MIT-BIH database, third and fifth columns. It can be observed that the wearable node accurately estimates the RR interval mean, i.e., around 99.6% of accuracy. For the standard deviation σ, a lower accuracy, i.e., 83.6%, was obtained for two reasons, (i) the relatively low sampling rate gave a sensibility of 8 ms, which can affect the measurement of small quantities such as the standard deviation, and (ii) failures in the peak finding algorithm also affected the measurement. A higher sampling rate and outlier detection techniques can be used to enhance the standard deviation measurement.

TABLE 1

Results for heart-rate (HR) with R and RR method.

| Trace | 6 s R [bpm] | 6 s RR [bpm] | Ref HR [bpm] |
|---|---|---|---|
| 16265 | 100 | 97 | 96 |
| 16272 | 60 | 62 | 62 |
| 16273 | 100 | 97 | 95 |
| 16420 | 90 | 94 | 95 |
| 16483 | 100 | 97 | 97 |
| 16539 | 80 | 80 | 79 |
| 16773 | 70 | 74 | 75 |
| 16786 | 70 | 72 | 71 |
| 16795 | 70 | 67 | 65 |
| 17052 | 70 | 68 | 69 |

TABLE 2

Results for RR interval mean and std. deviation σ.

| Trace | [s] | σ [s] | Ref. [s] | Ref. σ [s] |
|---|---|---|---|---|
| 16265 | 0.62 | 0.62 | 0.016 | 0.019 |
| 16272 | 0.96 | 0.96 | 0.109 | 0.115 |
| 16273 | 0.64 | 0.64 | 0.023 | 0.049 |
| 16420 | 0.63 | 0.63 | 0.015 | 0.018 |
| 16483 | 0.62 | 0.62 | 0.015 | 0.012 |
| 16539 | 0.74 | 0.75 | 0.062 | 0.054 |
| 16773 | 0.79 | 0.79 | 0.056 | 0.058 |
| 16786 | 0.85 | 0.84 | 0.046 | 0.036 |
| 16795 | 0.91 | 0.92 | 0.070 | 0.069 |
| 17052 | 0.85 | 0.85 | 0.047 | 0.047 |

Accelerometer Processing. Ten 3-dimensional accelerometer traces were recorded with a sample rate of 60 Hz using Sensor Log, an iOS app that allows reading sensor data from the device, and exporting them in character-separated values (CSV) format. Sensor Log also provides information about the number of footsteps counted by the iOS device. This was used as a reference to evaluate the accuracy of the footstep counter application in the wearable node. Table 3 shows the footstep count estimated by the wearable node, second column, and compares this with the footstep estimate of the iOS device, third column, and real footstep number counted by the user while performing the steps, fourth column. The first column shows the trace name, which lists 3 walking traces, 3 running traces and 3 stair climbing traces, i.e., downward, upwards and down/upwards. It can be observed that, in average, the wearable node counted footsteps with the same accuracy of the iOS device, i.e., approximately 94% with respect to the number of steps counted by the user.

TABLE 3

Evaluation results for footstep counter.

| Trace | Node | iOS | Real |
|---|---|---|---|
| walk 0 | 44 | 49 | 46 |
| walk 1 | 39 | 39 | 40 |
| walk 2 | 48 | 48 | 50 |
| walk 3 | 38 | 39 | 40 |
| run 0 | 32 | 33 | 34 |
| run 1 | 37 | 42 | 40 |
| run 2 | 32 | 33 | 32 |
| climb up | 19 | 19 | 18 |
| climb down | 17 | 18 | 18 |
| climb do up | 34 | 34 | 39 |

6. Internet of Medical Things

Figure 15:
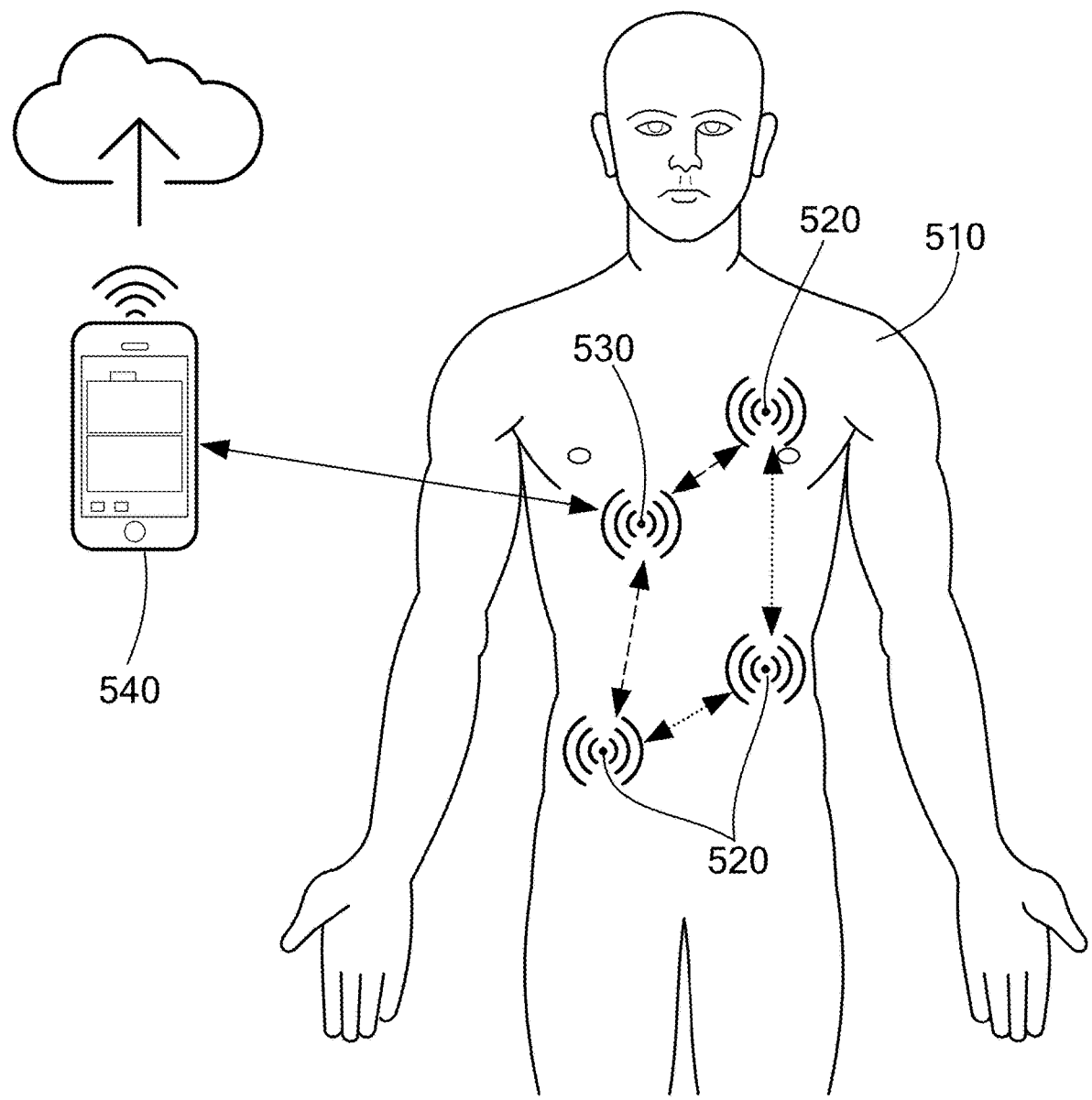
FIG. 15 is a schematic illustration of a system configuration in which multiple implantable nodes are connected to the Internet.

FIG. 15 shows an embodiment of a system configuration in which multiple implantable nodes 520 communicate both inside a body 510 (shown by dotted lines) and also with a gateway node 530 deployed on the body (shown by dashed lines). The gateway node can route any information to an access point node 540 (shown by a continuous line), which in this scenario is implemented in a smartphone connected to the Internet. The system can include aspects of the ultrasonic communication system described above, which will not be repeated in detail in the following description.

6.1 Implantable Node

As noted above, an implantable node can include an ultrasonic sensing and/or actuating device that is deployed inside the body to measure one or more biological parameters and/or to perform operations, such as stimulating, pacing, and drug injection.

6.1.1 Hardware

The implantable node can embody several aspects. In one aspect, the implantable node can be a flexible sensing/processing/networking platform. Functionalities, such as communications, networking, sensing/actuation, and processing, can be reconfigurable and software-defined. In another aspect, the implantable node can use a small and compact form factor compatible with the state of the art in chip integration and with the desired functionalities. For example, in some embodiments, the implantable node can be implemented in a small disk of one centimeter diameter. In another aspect, the implantable node can be made of ultra-low-power, highly integrated, and reprogrammable components. In a further aspect, the implantable node can include ultrasonic wireless recharging and energy harvesting capabilities. For example, the implantable node can embed miniaturized ultrasonic transducers as transceivers and energy harvesters.

Figure 16:
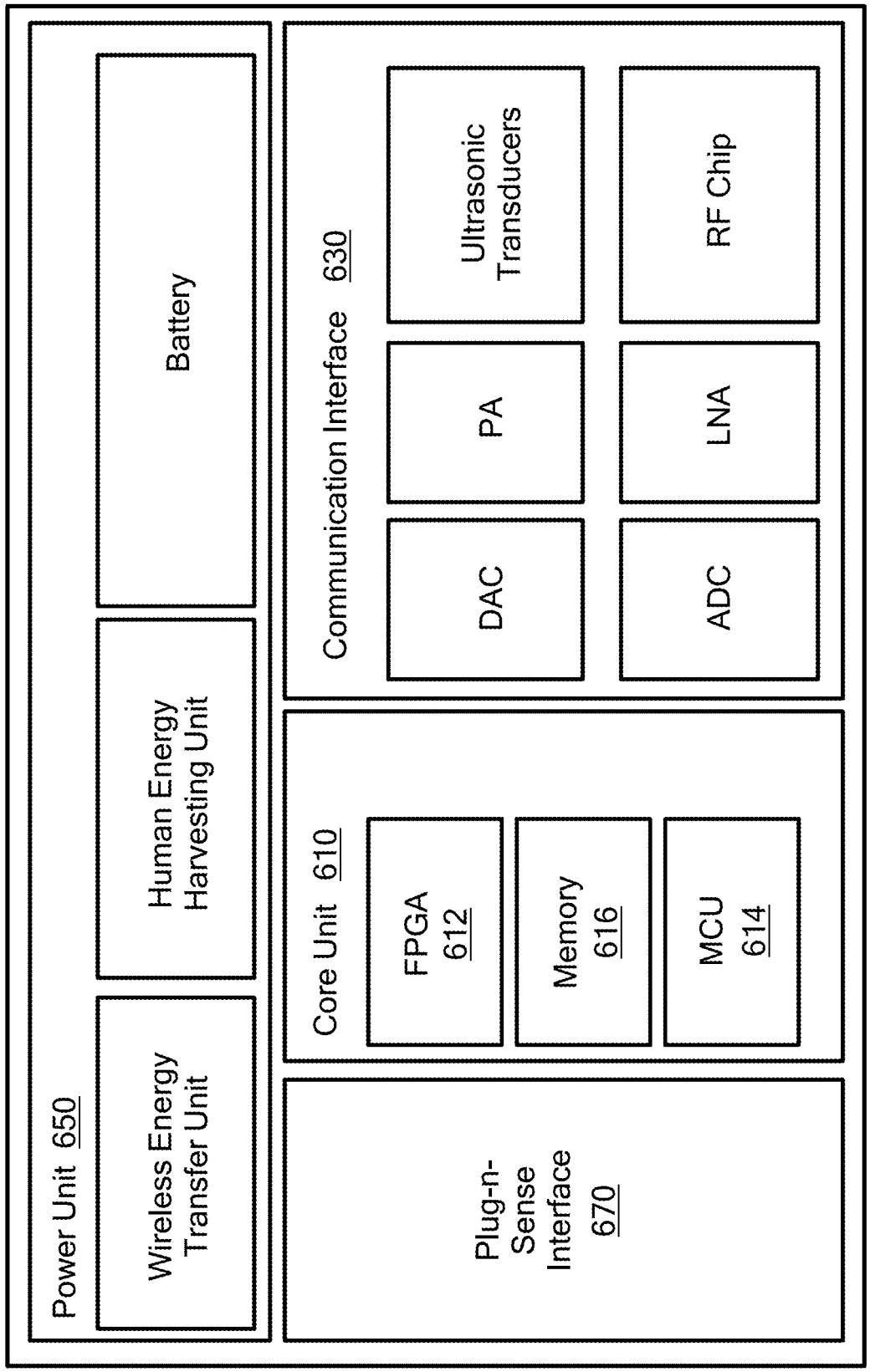
FIG. 16 is a schematic illustration of an implantable node hardware architecture.

FIG. 16 shows a high-level functional architecture of a hardware embodiment of an implantable node. The hardware can include a core unit 610, a communication interface 630, a power unit 650, and an interface 670 for a sensing and/or actuating unit, also termed a plug-n-sense interface.

In some embodiments, the core unit of the implantable node can include a mm-sized low-power field programmable gate array (FPGA). An FPGA enables flexible hardware reconfiguration in support of different physical layer protocols and experimentation with processing without sacrificing the energy efficiency. The core unit can include a micro controller unit (MC U). The combination of an FPGA and an MCU can offer hardware and software reprogrammability with small packaging and low energy consumption. The implantable node includes an interface for sensors and/or actuators. A flexible "plug-n-sense" interface can be used to accommodate different sensing and actuation units without reconfiguration or user intervention. For example, pressure and glucose level sensors, or leads for electrical stimulations can be used. Communication through ultrasounds and acoustic energy harvesting can be enabled by embedded miniaturized transducers. The implantable node can also embed an array of ultrasonic transducers with high integration, high energy-conversion efficiency, as well as focusing and beamforming capabilities. The implantable node can be battery-powered, and can include energy harvesting through acoustic vibration and ultrasonic wireless energy transfer.

6.1.1.1 Core Unit

In some embodiments, the core unit 610 includes two mm-size low-power processing units, an MCU 614 and an FPGA 612, that can execute software-defined communication, processing, and networking functionalities, and a non-volatile memory 616 that can store data from sensors and enable FPGA reconfiguration. The miniaturized FPGA can host the physical (PHY) layer and some time-critical data link or medium access control (MAC) layer functionalities, and can help off-load computationally expensive operations from the MCU. Reconfigurability at the physical layer is useful in an experimental and research platform based on non-standard communication technology. In implantable commercial devices, reconfigurability of processing and PHY functionalities can also be useful, as implants may have a lifetime of 5-10 years or greater, while wireless standard chipsets may a lifetime of 1.5 years and can soon become outdated. The system can also use low static power consumption, ideally zero, when idle, and can be woken up on demand. The system can include enough logic cells to implement the communication functionalities. These requirements are coupled, and can be addressed in an integrated manner in the present system.

FPGA. The FPGA 612 can host the physical (PHY) layer functionalities, and can off-load some computationally expensive operations from the MCU. The FPGA enables hardware reconfigurability and can offer a level of flexibility that is useful in a research sensing platform. An embedded FPGA can be small, e.g., in the order of a few square millimeters, to reduce the occupied area of the printed circuit board (PCB). The FPGA can have low static power consumption, to minimize the energy consumption when the system is idle, e.g., no ongoing transmission or sensing. Moreover, the FPGA can offer enough hardware resources, e.g., logic cells or logic elements, to implement the communication and networking functionalities needed. These three requirements are coupled, and are preferably addressed in an integrated manner in the present system.

MCU. The implantable node MCU 614 is in charge of executing software-defined functionalities to implement flexible and reconfigurable upper-layer protocols, e.g., MAC, Network, Transport and Application. Small packages, e.g., on the order of a few square millimeters, and low-power consumption are requirements that can be addressed in the system. However, size and energy consumption can be traded for performance, to be able to easily implement relatively complex protocols and control algorithm on a real-time operative system (RTOS).

6.1.1.2 Communication Interface

In some embodiments, the communication interface 630 enables ultrasonic wireless connectivity through data converters, power and low noise amplifiers, and transducers. The communication interface includes a receiver (Rx) chain and a transmitter (Tx) chain. The Rx chain includes a low-noise amplifier and an analog-to-digital converter (ADC) to amplify and digital-convert the received signals. The Tx chain can include a digital-to-analog converter (DAC) and a power amplifier to analog-convert and amplify the digital waveforms before transmission. Tx and Rx chains can be in charge to transmit and receive data through the ultrasonic transducers. The communication between the core unit and the communication interface can be performed through serial or parallel communications.

Data Converters. Data converters, i.e., analog to digital converters (ADC) and digital to analog converters (DAC), are used to analog-to-digital convert the received signal in the receiver chain, and to digital-to-analog convert the digital waveform before transmission in the transmitter chain, respectively. The ADC and DAC components can be selected based on the communication requirements of the implantable node.

Amplification Stage. The amplification stage can include a low noise amplifier (LNA) in the receiver chain and a power amplifier (PA) in the transmitter chain. Selecting the right amplification components can be based on consideration of several factors. First, the communication requirements discussed above, i.e., signal bandwidth and central frequency, constrain the frequency response of the amplifiers. Second, the characteristics of the ultrasonic transducers in use, e.g., sensitivity and transmission response, affect the amplification gain requirements. Third, the intended communication range, which depends on the specific application scenario, also affects the power and gain requirements. Fourth, the power consumption and the PCB area occupancy should be minimized.

At the receiver side, the high output impedance (on the order of 100 MΩ) of ultrasonic transducers makes the operational amplifiers (op-amp), whose input impedance is in the order of GΩ), suitable for use as receiver amplifiers. Moreover, since the received signals usually have a wide dynamic range, noise can be a concern. The noise floor of the transducer and the amplifier together limits the sensitivity of the receiver.

At the transmitter side, the high input capacitance of the ultrasonic transducers represents a challenge in driving the transducers. In fact, the amplifier output resistance, in conjunction with a capacitive load, forms an additional pole in the amplifier's transfer function that can cause instability, e.g., oscillations or peaks in the frequency response. Some amplifiers have inherently capacitive-load-drive capability, but in general, for high capacitance values, a compensation technique, e.g., matching circuits, can be employed. Alternatively, when higher transmission power is needed, the high input impedance of the transducers can require voltage input higher than the voltage supply, which in a battery powered design can be between 1.8 V and 5 V. In this case, the implantable node can embed charge-pump circuitry, i.e., circuits that use capacitors to store energy, to generate voltages that exceed the voltage supply.

Ultrasonic Transducer. Ultrasounds are mechanical pressure waves that propagate through elastic media at frequencies above the upper limit of human hearing, about 20 kHz. An ultrasonic transducer is a device that converts electrical signals into ultrasonic signals and vice versa. In some embodiments, the ultrasonic transducer can be piezoelectric or electrostatic, based on the physical mechanism that enables the conversion. A piezoelectric transducer produces a mechanical vibration through a thin piezoelectric element under an external voltage variation, and produces a voltage variation under an external mechanical vibration. In an electrostatic transducer the, fundamental mechanism is the vibration of a thin plate under electrostatic forces. Micromachined ultrasonic transducers can be used to provide small size and to control the matching of acoustic impedances.

In some embodiments, the system can also comprise an array of transducers to enable directional communications with spatial filtering capabilities, i.e., beamforming. Ultrasonic arrays are transducers with multiple and independent active elements. By delaying in time the signal transmitted by each array element, an ultrasonic beam can be steered towards a specific direction, while at the receiver, spatial filtering can be used to receive the signal coming from a preferred direction while suppressing other directions. This process, known as beamforming, can be leveraged to dynamically adapt the transducer radiation pattern.

RF Redundant Chip. The implantable node can embed a RF transceiver that can be used to offer redundancy to the system in case the low-power ultrasonic communications are not available, e.g., the gateway node is not correctly deployed. The RF chip can be operated in the industrial, scientific and medical (ISM) radio bands as well as in the Medical Implant Communication Service (MICS) band. The RF chip can implement Bluetooth, Wi-Fi or ZigBee functionalities, as well as proprietary communication schemes and protocols. The RF chip can be activated in emergency conditions and can enable long-range wireless communication that can connect the implantable node directly to the Internet access point.

6.1.1.3 Sensing and/or Actuating Unit Interface

In some embodiments, the implantable node can include a flexible interface system 670 to accommodate different sensing or actuating units, e.g., pressure and glucose level sensors, and actuating units, e.g., leads for electrical stimulations or micro-needles. The implantable node board can employ small pin headers where different detachable and interchangeable boards, i.e., daughter boards, can be connected. Each daughter board can accommodate different sensing or actuating units, making the implantable node a flexible sensing and actuating medical platform operable with many applications. The communication between the implantable node main board and the daughter boards can be handled by the MCU or the FPGA through serial or parallel connections. It will also be appreciated that a sensing and/or actuating unit can be hard wired to the implantable node.

Sensing units can include, for example and without limitation, a motion sensor, a gyroscope, an accelerometer, a cardiac rhythm monitor, a heart rate monitor, a pulse monitor, a blood pressure sensor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, and a sensor for pH, ionic strength or osmolality. The sensor for one or more biomolecules can be a sensor for one or more peptides, oligopeptides, polypeptides, proteins, glycoproteins, antibodies, antigens, nucleic acids, nucleotides, oligonucleotides, polynucleotides, sugars, disaccharides, trisaccharides, oligosaccharides, polysaccharides, lipids, glycolipids, proteolipids, cytokines, hormones, neurotransmitters, metabolites, glycosaminoglycans, and proteoglycans.

Actuating units can include, for example and without limitation, a drug pump, a heart stimulator, a heart pacemaker, a bone growth stimulator, a deep brain stimulator, a neurostimulator, and a neuromuscular electrical stimulator.

6.1.1.4 Power Unit

In some embodiments, the power unit 650 can accommodate a battery element to power the device. For some embodiments that employ low-power and low-voltage components, a small and thin battery with nominal voltage between 1.5 to 3 V can be used. The power unit can also embed two integrated circuits that manage the human energy harvesting and ultrasonic energy transferring functionalities. The former allows the harvesting of vibrational energy available in the body, e.g., heart beat or human voice reverberations. The latter allows the collection of energy from ultrasonic waves transferred from an out-the-body ultrasonic source.

6.1.2 Software

Figure 17:
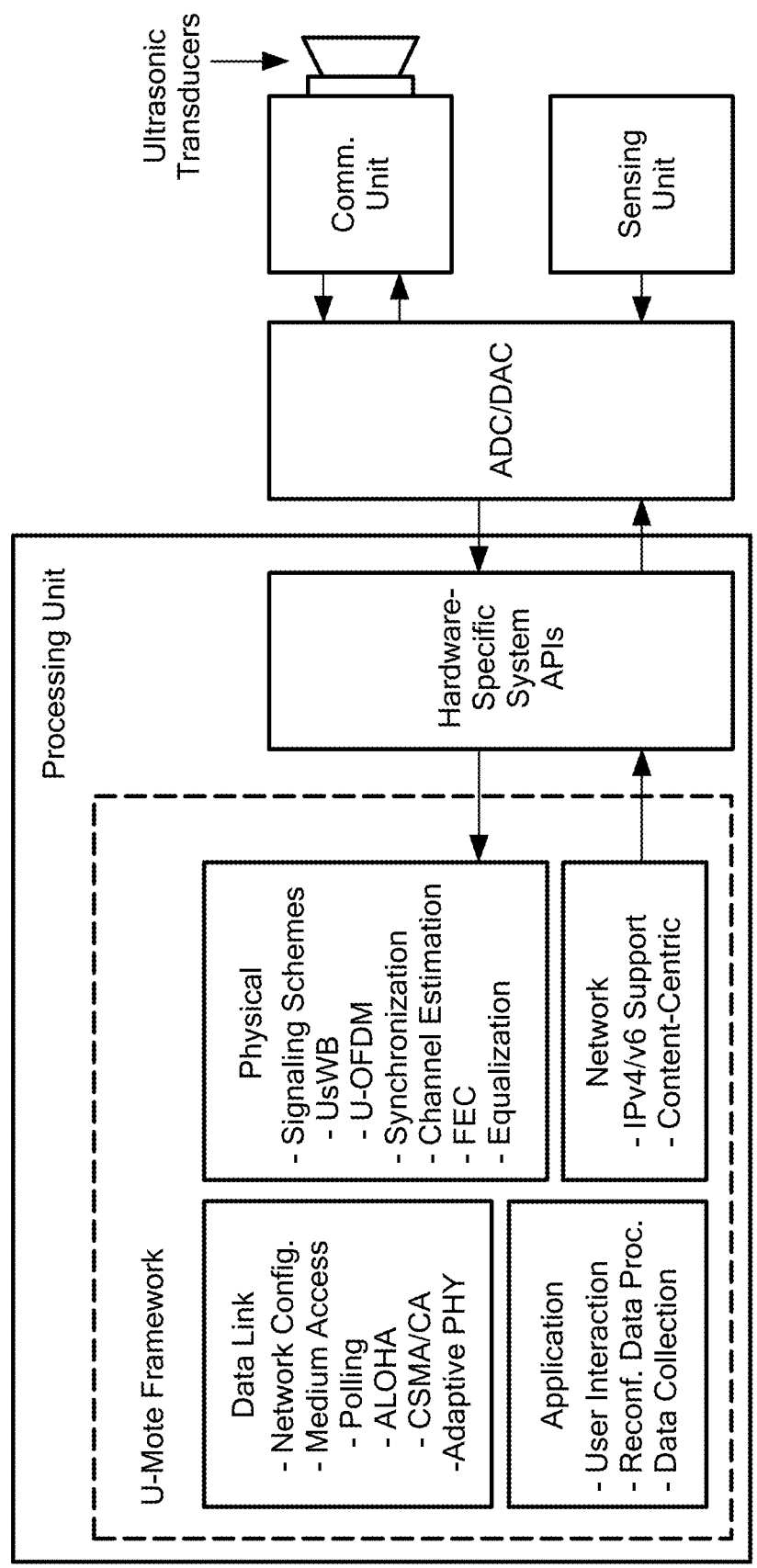
FIG. 17 is a schematic illustration of an overview of an implantable node networking framework.

The implantable node software architecture can include a software-defined networking framework that encloses a set of PHY, data link and network layer functionalities that can flexibly adapt to the application and system requirements to efficiently distribute information. The implantable node framework can also offer real-time reconfigurability at the application layer to provide a flexible platform to develop medical applications. In particular, sensor data processing applications running in the nodes can be decomposed into primitive building blocks that can be arbitrarily arranged to create new sensing applications that fit user requirements. FIG. 17 shows a high-level overview of the framework, substantially similar to FIG. 2 described above. It can include (i) PHY layer functionalities, including modulation and synchronization, for impulsive transmissions, (ii) data link layer functionalities including forward error control and medium access control (MAC) protocols, (iii) network layer functionalities, e.g., IPv4 and IPv6 support and content-centric networking, and (iv) application layer functionalities, i.e., reconfigurable sensing data processing and user interface. In some embodiments, these functionalities can be split into two different processing units. The data link, networking and application layer functionalities can be run on the MCU, and computationally demanding operations can be offloaded to the FPGA.

IP Integration. The implantable node networking framework provides interoperability with the Internet by defining an adaptation layer that integrates IPv4 and IPv6 protocol support. The adaptation layer includes a set of functionalities that interface the traditional IP network layer with the implantable node MAC layer through IP header compression and IP packet fragmentation functions optimized for ultrasonic networks. Standard protocols, such as TCP or UDP, or custom protocols can be implemented at a transport layer.

Figure 18:
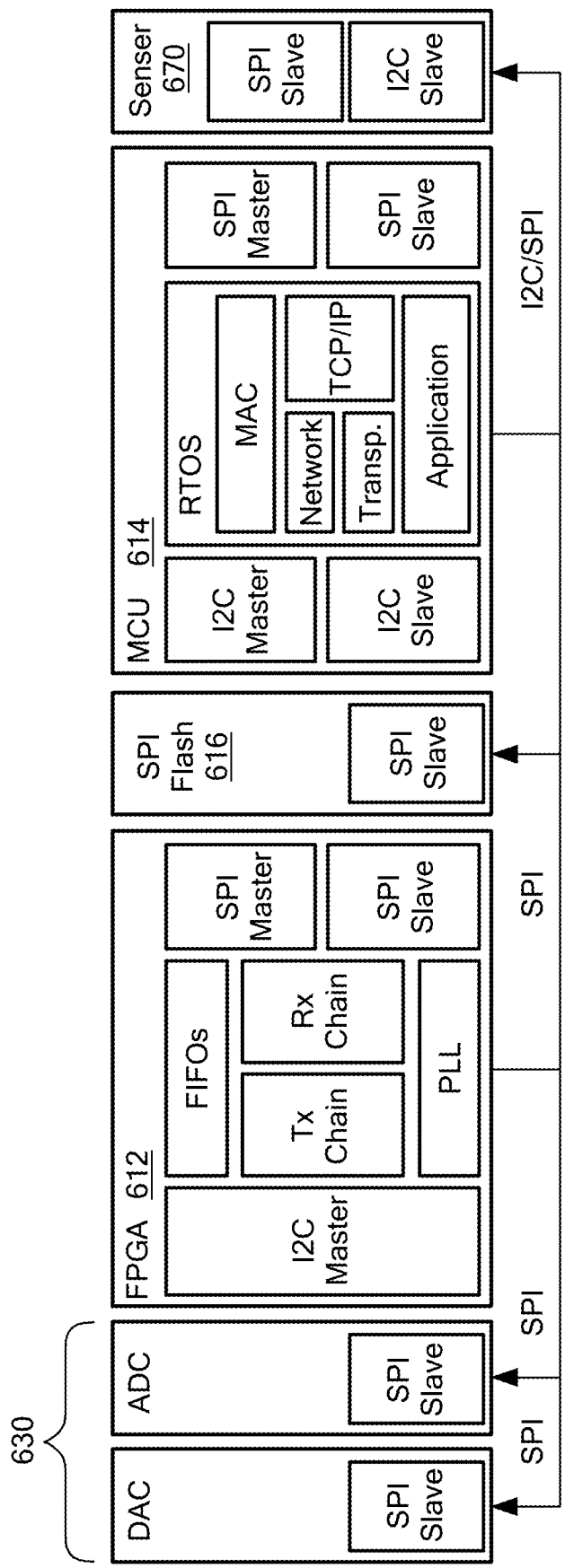
FIG. 18 is a schematic illustration of an implantable node software architecture.

FIG. 18 shows an embodiment in which the implantable node software architecture is split between the FPGA 612 and MCU 614. The FPGA logic design implements the PHY layer communication functionalities, as well as the interfaces, e.g., SPI and I2C, to connect the FPGA chip with the MCU and the peripherals (DAC, ADC, memory and sensors). The MCU software design can be based on a real-time operative system (RTOS) and can execute the upper layer communication functionalities and protocol. The MCU software design can also define interfaces, e.g., SPI and I2C, to enable data exchange between the MCU and the peripherals (FPGA, DAC, ADC, memory and sensors).

6.1.2.1 FPGA Logic Design

The FPGA top-level module can instantiate Tx and Rx chain blocks that implement the PHY layer communication functionalities, a set of first-in-first-out (FIFO) memory queue blocks, and finally a phase-locked loop (PLL) block. The logic is driven by an external system clock signal input to one of the FPGA's pin.

Tx/Rx Chain. The Tx and Rx chain blocks implement the transmitter and receiver PHY layer functionalities, respectively. This block gets as input a stream of bytes coming from the MCU though SPI, and outputs the PHY digital waveforms representing the modulated bits. The digital waveforms are then passed to the DAC through SPI, digital-to-analog converted, amplified by the PA, and then transmitted from the ultrasonic transducers.

On the receiver side, the signal captured by the receiver ultrasonic transducers is first amplified by the LNA and then analog-to-digital converted by the ADC. The digital waveforms are input through SPI to the Rx chain. This block can perform on the input waveforms digital signal processing operations such synchronization, channel estimation, and demodulation. The output of this block will be a stream of bytes that can then be passed to the MCU via SPI.

Both the Tx chain and the Rx chain can run computationally complex operations, e.g., correlations, fast-Fourier transforms (FFTs), or digital filtering, among others, which are needed to implement PHY layer functionalities.

FIFOs. The FIFO blocks implement first-in-first-out memory queues that allow the storage and retrieval of ordered data. In one embodiment, FIFO blocks can buffer data coming in and out of the FPGA from and to the external peripherals and the MCU, before being processed by the functional logic. FIFOs may also be used to handle multi-clock domain data exchange, i.e., data flowing between logics driven by clock signals with different frequencies.

PLL. The phase-locked loop (PLL) module allows synthesizing clock signals with a higher or lower frequency than the system clock.

6.1.2.2 MCU Software

The MCU software architecture implements the upper layer networking functionalities and protocols. The software design is based on a real-time operating system (RTOS) that provides real-time performance and at the same time can offer a small and configurable footprint. Specifically, the desired RTOS runs in a resource constrained environment. The RTOS can offer low-power functionalities, and can support SPI and I2C drivers to enable communications with the external peripherals (FPGA, DAC, ADC, memory and sensors). The RTOS can integrate the TCP/IP stack to enable the implantable node to support internet-of-things (IoT) applications. The RTOS can run application layer processing related to sensing or actuating operations. A number of commercial or open source RTOSs can be used, such as FreeRTOS or uTasker.

6.2 Gateway Node

The ultrasonic gateway nodes are deployed along a body to bridge the intra-body network of implantable node with the external world. The gateway nodes can also accommodate sensing capabilities if required, e.g., electrocardiogram leads.

6.2.1 Hardware

The gateway node hardware design can be similar to the implantable node hardware design except for a few different components. The gateway node can be a flexible sensing/processing/networking platform with a small and compact form factor, e.g., no more than two centimeters per side, that can offer low energy consumption, and that communicates wirelessly through ultrasounds and RF in body tissues and air. The gateway node can be packaged such to offer a slim form factor that can be attached to stick-on skin patches.

The hardware architecture of the gateway node can be similar to one of the implantable node shown in FIG. 16. The hardware design of the gateway node can be based on mm-sized and low-power field programmable gate arrays (FPGAs) or/and microcontroller units (MCUs) that offer hardware and software reprogrammability in small packages and low energy consumption. The gateway nodes can optionally offer sensing capabilities for measuring biomedical parameters measurable on the body surface, e.g., ECG signals. The communication through ultrasounds, both with the implantable node in body tissues and with the access point node in air, can be done by using miniaturized piezoelectric transducers. For example, in some embodiments, the gateway node can embed two arrays of miniaturized ultrasonic transducers that offer high integration, as well as focusing and beamforming capabilities that enhance the ultrasonic propagation in body tissues and in air. The two arrays are differently coupled with the external medium to support communication in air and in body tissues, respectively. The gateway node also can embed a low-power RF transceiver that enables communication via RF with the access point node. The gateway node is powered by a small and thin rechargeable battery that can be recharged after detaching the node from the body. The gateway node can also provide human energy harvesting or ultrasonic wireless energy transfer functionalities that help prolonging the device battery life.

6.2.1.1 Communication Interface

The communication interface enables ultrasonic wireless connectivity through data converters, power and low noise amplifiers, and transducers. The communication interface includes two receiver (Rx) and two transmitter (Tx) chains. The Rx chains can include a low-noise amplifier and an analog-to-digital converter (ADC) to amplify and digital-convert the received signals. The Tx chain can include a digital-to-analog converter (DAC) and a power amplifier to analog-convert and amplify the digital waveforms before transmission. Tx and Rx chains can be in charge to transmit and receive data through the ultrasonic transducers. The first Tx/Rx chain pair is used for the in-tissue communication with the implantable nodes, while the second Tx/Rx chain pair is used for the in-air communication with the access point nodes. The communication between the core unit and the communication interface can be performed through serial or parallel communications.

RF Transceiver The gateway node can also embed a low-power RF transceiver that enables communication via RF with the access point node. The RF chip can operate in the industrial, scientific and medical (ISM) radio band as well as in the Medical Implant Communication Service (MICS) band. The RF chip can implement wireless short range or local area network communication standards, such as Bluetooth, Wi-Fi or ZigBee, as well as proprietary communication schemes and protocols.

6.2.1.2 Power Unit

The power unit can accommodate a battery element to power the device. The power unit of the gateway node can also embed a ultrasonic power transmission unit to wirelessly transfer ultrasonic energy to the implantable nodes.

6.3 Access Point Node

The access point node can be deployed around the body and bridge the system with the Internet. The access point node can be a standalone device, i.e., a wireless or wired box deployed around the patient, that connects wirelessly or through wires to an Internet access point, or it can be implemented via software on a smart device such a tablet or smartphone.

The access point node can provide multiple communication interfaces. A wireless or wired communication interface connects the access point node with the Internet, e.g., Wi-Fi or Ethernet. Two wireless interfaces connect the access point node with the gateway nodes through in-air ultrasonic waves and in-air RF waves. The access point node operates as a sensing sink and as Internet gateway. The access point node collects the data coming from the gateway nodes, processes and compresses them and then sends them to the cloud via Internet. Similarly, the access point node can receive remote control commands and can forward them to the gateway nodes and then to the implantable node.

The sensor and/or actuating unit 80 can employ a variety of sensors to sense biological parameters or actuators to actuate biological or medical procedures.

In some embodiments, a sensor can comprise a motion sensor, a gyroscope, an accelerometer, a cardiac rhythm monitor, a heart rate monitor, a pulse monitor, a blood pressure sensor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, or a sensor for pH, ionic strength or osmolality.

In some embodiments, the sensor for one or more biomolecules can comprise a sensor for one or more peptides, oligopeptides, polypeptides, proteins, glycoproteins, antibodies, antigens, nucleic acids, nucleotides, oligonucleotides, polynucleotides, sugars, disaccharides, trisaccharides, oligosaccharides, polysaccharides, lipids, glycolipids, proteolipids, cytokines, hormones, neurotransmitters, metabolites, glycosaminoglycans, and proteoglycans.

Is some embodiments, the actuator can comprise a drug pump, a heart stimulator, a heart pacemaker, a bone growth stimulator, a deep brain stimulator, a neurostimulator, or a neuromuscular electrical stimulator.

The system and method described herein can be used with humans and non-human animals and can be used in medical and veterinary fields.

The processing unit and communication unit described herein can be part of a computer system that executes programming for controlling the system for transmitting data ultrasonically among wearable devices as described herein. The computing system can be implemented as or can include a computing device that includes a combination of hardware, software, and firmware that allows the computing device to run an applications layer, including the application layer described above, or otherwise perform various processing tasks. Computing devices can include without limitation personal computers, work stations, servers, laptop computers, tablet computers, mobile devices, hand-held devices, wireless devices, smartphones, wearable devices, smart watches, smart clothing, embedded devices, microprocessor-based devices, microcontroller-based devices, programmable consumer electronics, mini-computers, main frame computers, and the like.

The computing device can include a basic input/output system (BIOS) and an operating system as software to manage hardware components, coordinate the interface between hardware and software, and manage basic operations such as start up. The computing device can include one or more processors and memory that cooperate with the operating system to provide basic functionality for the computing device. The operating system provides support functionality for the applications layer and other processing tasks. The computing device can include a system bus or other bus (such as memory bus, local bus, peripheral bus, and the like) for providing communication between the various hardware, software, and firmware components and with any external devices. Any other type of architecture or infrastructure that allows the components to communicate and interact with each other can be used.

Processing tasks can be carried out by one or more processors. Various types of processing technology can be used, including a single processor or multiple processors, a central processing unit (CPU), multicore processors, parallel processors, or distributed processors. Additional specialized processing resources such as graphics (e.g., a graphics processing unit or GPU), video, multimedia, or mathematical processing capabilities can be provided to perform certain processing tasks. Processing tasks can be implemented with computer-executable instructions, such as application programs or other program modules, executed by the computing device. Application programs and program modules can include routines, subroutines, programs, drivers, objects, components, data structures, and the like that perform particular tasks or operate on data.

Processors can include one or more logic devices, such as small-scale integrated circuits, programmable logic arrays, programmable logic device, masked-programmed gate arrays, field programmable gate arrays (FPGAs), and application specific integrated circuits (ASICs). Logic devices can include, without limitation, arithmetic logic blocks and operators, registers, finite state machines, multiplexers, accumulators, comparators, counters, look-up tables, gates, latches, flip-flops, input and output ports, carry in and carry out ports, and parity generators, and interconnection resources for logic blocks, logic units and logic cells.

Although certain embodiments are described above utilizing FPGAs, it will be appreciated that other logic devices, including programmable logic devices and application specification integrated circuits (ASICs) can be used in some embodiments.

The computing device includes memory or storage, which can be accessed by the system bus or in any other manner. Memory can store control logic, instructions, and/or data. Memory can include transitory memory, such as cache memory, random access memory (RAM), static random access memory (SRAM), main memory, dynamic random access memory (DRAM), and memristor memory cells. Memory can include storage for firmware or microcode, such as programmable read only memory (PROM) and erasable programmable read only memory (EPROM). Memory can include non-transitory or nonvolatile or persistent memory such as read only memory (ROM), memory chips, and memristor memory cells. Non-transitory memory can be provided on an external storage device. A computer-readable medium can include any physical medium that is capable of encoding instructions and/or storing data that can be subsequently used by a processor to implement embodiments of the method and system described herein. Any other type of tangible, non-transitory storage that can provide instructions and/or data to a processor can be used in these embodiments.

The computing device can include one or more input/output interfaces for connecting input and output devices to various other components of the computing device. Input and output devices can include, without limitation, keyboards, mice, joysticks, microphones, displays, touch-screens, monitors, scanners, speakers, and printers. Interfaces can include universal serial bus (USB) ports, serial ports, parallel ports, game ports, and the like. Other hardware components and devices can interface with the computing device. As used herein, the term "transceiver" can include one or more devices that both transmit and receive signals, whether sharing common circuitry, housing, or a circuit board, or whether distributed over separated circuitry, housings, or circuit boards, and can include a transmitter-receiver.

The computing device can access a network over a network connection that provides the computing device with telecommunications capabilities. Network connection enables the computing device to communicate and interact with any combination of remote devices, remote networks, and remote entities via a communications link. The communications link can be any type of communication link, including without limitation a wired or wireless link. For example, the network connection can allow the computing device to communicate with remote devices over a network, which can be a wired and/or a wireless network, and which can include any combination of intranet, local area networks (LANs), enterprise-wide networks, medium area networks, wide area networks (WANs), the Internet, cellular networks, and the like. Control logic and/or data can be transmitted to and from the computing device via the network connection.

The computing device can include a browser and a display that allow a user to browse and view pages or other content served by a web server over the communications link. A web server, server, and database can be located at the same or at different locations and can be part of the same computing device, different computing devices, or distributed across a network. A data center can be located at a remote location and accessed by the computing device over a network.

As used herein, "consisting essentially of" allows the inclusion of materials or steps that do not materially affect the basic and novel characteristics of the claim. Any recitation herein of the term "comprising," particularly in a description of components of a composition or in a description of elements of a device, can be exchanged with "consisting essentially of" or "consisting of."

It will be appreciated that the various features of the embodiments described herein can be combined in a variety of ways. For example, a feature described in conjunction with one embodiment may be included in another embodiment even if not explicitly described in conjunction with that embodiment.

The present invention has been described in conjunction with certain preferred embodiments. It is to be understood that the invention is not limited to the exact details of construction, operation, exact materials or embodiments shown and described, and that various modifications, substitutions of equivalents, alterations to the compositions, and other changes to the embodiments disclosed herein will be apparent to one of skill in the art.

What is claimed is:

1. A system for transmitting signals among a network of implantable and wearable devices, comprising:
    an implantable node, implantable in a body, comprising:
        a sensing unit operative to sense a biological parameter or an actuating unit operative to actuate a biological procedure,
        a communication unit including an ultrasonic communication interface operative to transmit and receive ultrasonic signals through biological tissue and optionally through air, and a core unit in communication with the communication unit and with the sensing unit or actuating unit;

a gateway node, wearable on the body, comprising:
a communication unit including an ultrasonic communication interface operative to transmit and receive ultrasonic signals through biological tissue and optionally through air, and
a core unit in communication with the communication unit;

wherein the communication unit of at least one of the implantable node and the gateway node further includes a radio frequency interface operative to transmit and receive radio frequency signals through biological tissue or through air; and an access point node including a communication interface operative to transmit and receive signals through air or through biological tissue with the gateway node, the implantable node, or both the gateway node and the implantable node.

2. The system of claim 1, wherein the communication interface of the access point node is operative to transmit and receive radio frequency signals through air or through biological tissue.

3. The system of claim 1, wherein the communication interface of the access point node is operative to transmit and receive ultrasonic signals through air or through biological tissue.

4. The system of claim 1, wherein the communication interface of the access point node is operative to transmit and receive radio frequency signals through air or through biological tissue and to transmit and receive ultrasonic frequency signals through air or through biological tissue.

5. The system of claim 1, wherein the communication unit of the implantable node comprises an ultrasonic transceiver to transmit and receive ultrasonic communications and a radio frequency transceiver to transmit and receive radio frequency communications.

6. The system of claim 1, wherein the communication unit of the gateway node comprises an ultrasonic transceiver to transmit and receive ultrasonic communications and a radio frequency transceiver to transmit and receive radio frequency communications.

7. The system of claim 1, wherein the core unit of each of the implantable node and the gateway node comprises one or more logic devices to execute communication, processing, and networking tasks, the one or more logic devices including small-scale integrated circuits, programmable logic arrays, programmable logic device, masked-programmed gate arrays, field programmable gate arrays, or application specific integrated circuits.

8. The system of claim 1, wherein the core unit of each of the implantable node and the gateway node comprises a microcontroller unit, a programmable logic device, or both a microcontroller unit and a programmable logic device operative to execute communication, processing and networking tasks.

9. The system of claim 8, wherein the core unit of one or both of the implantable node and the gateway node includes one or both of a serial peripheral interface (SPI) and an inter integrated circuit (I2C) interface to control communications between the microcontroller, the programmable logic device, the communication unit, and memory.

10. The system of claim 8, wherein the microcontroller unit of one or both of the implantable node and the gateway node is operative at upper layers of a protocol stack to enable ultrasonic or radio frequency communication.

11. The system of claim 8, wherein the microcontroller of one or both of the implantable node and the gateway node is operative at the network layer to provide content centric addressing or IP header compression and IP Packet fragmentation.

12. The system of claim 8, wherein the programmable logic device of one or both of the implantable node and the gateway node is operative at a physical layer of a protocol stack to enable ultrasonic or radio frequency communication.

13. The system of claim 1, wherein the gateway node further comprises a sensing unit operative to sense a biological parameter or an actuating unit operative to actuate a biological procedure.

14. The system of claim 1, wherein the access point node is disposed on a computing device that includes an Internet connection.

15. The system of claim 1, wherein the communication interface of the access point node is operative to transmit and receive signals using a communication protocol including Bluetooth, Wi-Fi, or Zigbee.

* * * * *